(12) United States Patent
Morrison

(10) Patent No.: US 10,787,516 B2
(45) Date of Patent: Sep. 29, 2020

(54) ANTIBODIES THAT BIND TO AXL PROTEINS

(71) Applicant: AGENSYS, INC., Santa Monica, CA (US)

(72) Inventor: Karen Jane Meyrick Morrison, Santa Monica, CA (US)

(73) Assignee: AGENSYS, INC., Santa Monica, CA (US)

( * ) Notice: Subject to any disclaimer, the term of this patent is extended or adjusted under 35 U.S.C. 154(b) by 229 days.

(21) Appl. No.: 15/572,727

(22) PCT Filed: May 18, 2016

(86) PCT No.: PCT/US2016/033153
§ 371 (c)(1),
(2) Date: Nov. 8, 2017

(87) PCT Pub. No.: WO2016/187354
PCT Pub. Date: Nov. 24, 2016

(65) Prior Publication Data
US 2018/0134792 A1    May 17, 2018

Related U.S. Application Data

(60) Provisional application No. 62/163,264, filed on May 18, 2015.

(51) Int. Cl.
| | | |
|---|---|---|
| G01N 31/00 | (2006.01) | |
| G01N 33/53 | (2006.01) | |
| C07K 16/28 | (2006.01) | |
| G01N 33/574 | (2006.01) | |
| C07K 16/30 | (2006.01) | |
| A61K 39/00 | (2006.01) | |

(52) U.S. Cl.
CPC .......... *C07K 16/2863* (2013.01); *C07K 16/30* (2013.01); *G01N 33/574* (2013.01); *G01N 33/57492* (2013.01); *A61K 2039/505* (2013.01); *C07K 2317/21* (2013.01); *C07K 2317/54* (2013.01); *C07K 2317/55* (2013.01); *C07K 2317/56* (2013.01); *C07K 2317/565* (2013.01); *C07K 2317/622* (2013.01); *G01N 2333/705* (2013.01)

(58) Field of Classification Search
None
See application file for complete search history.

(56) References Cited

U.S. PATENT DOCUMENTS

| | | |
|---|---|---|
| 2005/0032175 A1 | 2/2005 | Stahl et al. |
| 2010/0166768 A1 | 7/2010 | Sleeman et al. |
| 2012/0058906 A1 | 3/2012 | Smider et al. |
| 2012/0195879 A1 | 8/2012 | Walker et al. |
| 2012/0282637 A1 | 11/2012 | Huber et al. |
| 2014/0121126 A1 | 5/2014 | Bivona et al. |
| 2014/0227283 A1 | 8/2014 | Robert et al. |
| 2014/0302041 A1 | 10/2014 | Robert et al. |

FOREIGN PATENT DOCUMENTS

| | | | |
|---|---|---|---|
| WO | WO 2009062690 A1 | 5/2009 | |
| WO | WO 2010130751 A1 | 11/2010 | |
| WO | WO 2011159980 A1 | 12/2011 | |
| WO | WO 2014068139 A1 | 5/2014 | |
| WO | WO-2016187356 A1 * | 11/2016 | ............. C07K 16/30 |
| WO | WO 2016187356 A1 | 11/2016 | |

OTHER PUBLICATIONS

Lloyd et al. 2009. Modelling the human immune response: performance of a 1011 human antibody repertoire against a broad panel of therapeutically relevant antigens. Protein Engineering, Design & Selection 22(3):159-168.*
Coleman et al. (Research in Immunology, 1994; 145(1): 33-36).*
Berclaz et al., 2001, "Estrogen dependent expression of the receptor tyrosine kinase axl in normal and malignant human breast," Ann Oncol., 12(6):819-824.
Cell Signaling Technology, 2014, "Axl (C89E7) Rabbit mAb—#8661," rev. Oct. 28, 2019, retreived from internet: https://media.cellsignal.com/pdf/8661.pdf on Dec. 22, 2019 (2 pages).
Chung et al., 2003, Expression of the proto-oncogene Axl in renal cell carcinoma, DNA Cell Biol., 22(8):533-540.
Craven et al., 1995, "Receptor tyrosine kinases expressed in metastatic colon cancer," Int J Cancer, 60(6):791-797.
Giles et al., 2013, "Axl mediates acquired resistance of head and neck cancer cells to the epidermal growth factor receptor inhibitor erlotinib," Mol Cancer Ther., 12(11):2541-2558.
Ito et al., 1999, "Expression of the Axl receptor tyrosine kinase in human thyroid carcinoma," Thyroid, 9(6):563-567.
NCBI_S24700, 2000, "Ig heavy chain V6 region—human," NCBI Accession No. S24700, Jan. 21, 2000. Retrieved from the internet: www.ncbi.nlm.nih.gov/protein/S24700?report=genpept on Jul. 20, 2016 (1 page).
O'Bryan et al., 1995, "The transforming receptor tyrosine kinase, Axl, is post-translationally regulated by proteolytic cleavage," J Biol Chem., 270(2):551-557.
R&D Systems, "Human Axl Antibody, Antigen Affinity-purified Polyclonal Goat IgG, Catalog No. AF154," rev. Feb. 6, 2018, retreived from internet: https://resources.rndsystems.com/pdfs/datasheets/af154.pdf on Dec. 22, 2019 (2 pages.).
Sainaghi et al., 2005, "Gas6 induces proliferation in prostate carcinoma cell lines expressing the Axl receptor," J Cell Physiol., 204(1):36-44.

(Continued)

Primary Examiner — Lisa V Cook
(74) Attorney, Agent, or Firm — Jones Day

(57) ABSTRACT

Antibodies that bind to AXL protein and variants thereof are described herein. AXL exhibits a distinct and limited expression pattern in normal adult tissue(s), and is aberrantly expressed in the cancers listed in Table I. Consequently, the MAbs of the invention provide a diagnostic composition for the treatment and management of cancer.

18 Claims, 16 Drawing Sheets
Specification includes a Sequence Listing.

(56) References Cited

OTHER PUBLICATIONS

Shieh et al., 2005, "Expression of axl in lung adenocarcinoma and correlation with tumor progression," Neoplasia, 7(12):1058-1064.
Sievers et al., 1999, "Selective ablation of acute myeloid leukemia using antibody-targeted chemotherapy: a phase I study of an anti-CD33 calicheamicin immunoconjugate," Blood, 93(11):3678-3684.
Sun et al., 2004, "Coexpression of Gas6/Axl in human ovarian cancers," Oncology, 66(6):450-457.
Wu et al., 2002, "Clinical significance of AXL kinase family in gastric cancer," Anticancer Res., 22(2B):1071-1078.
Wu et al., 2014, "AXL kinase as a novel target for cancer therapy," Oncotarget, 5(20):9546-9563.
Ye et al., 2010, "An anti-Axl monoclonal antibody attenuates xenograft tumor growth and enhances the effect of multiple anti-cancer therapies," Oncogene, 29(38):5254-5264.
Zhang et al., 2012, "Activation of the AXL kinase causes resistance to EGFR-targeted therapy in lung cancer," Nat Genet., 44(8):852-860.
International Search Report and Written Opinion of International Patent Application No. PCT/US2016/033155 (Pub No. WO 2016187356) dated Aug. 18, 2016 (6 pages).

* cited by examiner

Fig. 1

```
   1  GGGAAGGAGGCAGGGGTGCTGAGAAGGCGGCTGCTGGGCAGAGCCGGTGGCAAGGGCCTC
  61  CCCTGCCGCTGTGCCAGGCAGGCAGTGCCAAATCCGGGGAGCCTGGAGCTGGGGGGAGGG
 121  CCGGGGACAGCCCGGCCCTGCCCCCTCCCCGCTGGGAGCCCAACAACTTCTGAGGAAAG
                  M   A   W   R   C   P   R   M   G   R   V   P   L   A   W   C   L  ·
 181  TTTGGCACCCATGGCGTGGCGGTGCCCCAGGATGGGCAGGGTCCCGCTGGCCTGGTGCTT
        ·  A   L   C   G   W   A   C   M   A   P   R   G   T   Q   A   E   E   S   P   F  ·
 241  GGCGCTGTGCGGCTGGGCGTGCATGGCCCCCAGGGGCACGCAGGCTGAAGAAAGTCCCTT
        ·  V   G   N   P   G   N   I   T   G   A   R   G   L   T   G   T   L   R   C   Q  ·
 301  CGTGGGCAACCCAGGGAATATCACAGGTGCCCGGGGACTCACGGGCACCCTTCGGTGTCA
        ·  L   Q   V   Q   G   E   P   P   E   V   H   W   L   R   D   G   Q   I   L   E  ·
 361  GCTCCAGGTTCAGGGAGAGCCCCCCGAGGTACATTGGCTTCGGGATGGACAGATCCTGGA
        ·  L   A   D   S   T   Q   T   Q   V   P   L   G   E   D   E   Q   D   D   W   I  ·
 421  GCTCGCGGACAGCACCCAGACCCAGGTGCCCCTGGGTGAGGATGAACAGGATGACTGGAT
        ·  V   V   S   Q   L   R   I   T   S   L   Q   L   S   D   T   G   Q   Y   Q   C  ·
 481  AGTGGTCAGCCAGCTCAGAATCACCTCCCTGCAGCTTTCCGACACGGGACAGTACCAGTG
        ·  L   V   F   L   G   H   Q   T   F   V   S   Q   P   G   Y   V   G   L   E   G  ·
 541  TTTGGTGTTTCTGGGACATCAGACCTTCGTGTCCCAGCCTGGCTATGTTGGGCTGGAGGG
        ·  L   P   Y   F   L   E   E   P   E   D   R   T   V   A   A   N   T   P   F   N  ·
 601  CTTGCCTTACTTCCTGGAGGAGCCCGAAGACAGGACTGTGGCCGCCAACACCCCCTTCAA
        ·  L   S   C   Q   A   Q   G   P   P   E   P   V   D   L   L   W   L   Q   D   A  ·
 661  CCTGAGCTGCCAAGCTCAGGGACCCCCAGAGCCCGTGGACCTACTCTGGCTCCAGGATGC
        ·  V   P   L   A   T   A   P   G   H   G   P   Q   R   S   L   H   V   P   G   L  ·
 721  TGTCCCCCTGGCCACGGCTCCAGGTCACGGCCCCCAGCGCAGCCTGCATGTTCCAGGGCT
        ·  N   K   T   S   S   F   S   C   E   A   H   N   A   K   G   V   T   T   S   R  ·
 781  GAACAAGACATCCTCTTTCTCCTGCGAAGCCCATAACGCCAAGGGGGTCACCACATCCCG
        ·  T   A   T   I   T   V   L   P   Q   Q   P   R   N   L   H   L   V   S   R   Q  ·
 841  CACAGCCACCATCACAGTGCTCCCCCAGCAGCCCCGTAACCTCCACCTGGTCTCCCGCCA
        ·  P   T   E   L   E   V   A   W   T   P   G   L   S   G   I   Y   P   L   T   H  ·
 901  ACCCACGGAGCTGGAGGTGGCTTGGACTCCAGGCCTGAGCGGCATCTACCCCCTGACCCA
        ·  C   T   L   Q   A   V   L   S   D   D   G   M   G   I   Q   A   G   E   P   D  ·
 961  CTGCACCCTGCAGGCTGTGCTGTCAGACGATGGGATGGGCATCCAGGCGGGAGAACCAGA
        ·  P   P   E   E   P   L   T   S   Q   A   S   V   P   P   H   Q   L   R   L   G  ·
1021  CCCCCCAGAGGAGCCCCTCACCTCGCAAGCATCCGTGCCCCCCCATCAGCTTCGGCTAGG
        ·  S   L   H   P   H   T   P   Y   H   I   R   V   A   C   T   S   S   Q   G   P  ·
1081  CAGCCTCCATCCTCACACCCCTTATCACATCCGCGTGGCATGCACCAGCAGCCAGGGCCC
        ·  S   S   W   T   H   W   L   P   V   E   T   P   E   G   V   P   L   G   P   P  ·
1141  CTCATCCTGGACCCACTGGCTTCCTGTGGAGACGCCGGAGGGAGTGCCCCTGGGCCCCCC
        ·  E   N   I   S   A   T   R   N   G   S   Q   A   F   V   H   W   Q   E   P   R  ·
1201  TGAGAACATTAGTGCTACGCGGAATGGGAGCCAGGCCTTCGTGCATTGGCAAGAGCCCCG
        ·  A   P   L   Q   G   T   L   L   G   Y   R   L   A   Y   Q   G   Q   D   T   P  ·
1261  GGCGCCCCTGCAGGGTACCCTGTTAGGGTACCGGCTGGCGTATCAAGGCCAGGACACCCC
        ·  E   V   L   M   D   I   G   L   R   Q   E   V   T   L   E   L   Q   G   D   G  ·
1321  AGAGGTGCTAATGGACATAGGGCTAAGGCAAGAGGTGACCCTGGAGCTGCAGGGGGACGG
        ·  S   V   S   N   L   T   V   C   V   A   A   Y   T   A   A   G   D   G   P   W  ·
```

Fig. 1 (continued)

```
1381 GTCTGTGTCCAATCTGACAGTGTGTGTGGCAGCCTACACTGCTGCTGGGGATGGACCCTG
      · S   L   P   V   P   L   E   A   W   R   P   G   Q   A   P   V   H   Q   L ·
1441 GAGCCTCCCAGTACCCCTGGAGGCCTGGCGCCCAGGGCAAGCACAGCCAGTCCACCAGCT
      · V   K   E   P   S   T   P   A   F   S   W   P   W   W   Y   V   L   L   G   A ·
1501 GGTGAAGGAACCTTCAACTCCTGCCTTCTCGTGGCCCTGGTGGTATGTACTGCTAGGAGC
      · V   V   A   A   A   C   V   L   I   L   A   L   F   L   V   H   R   R   K   K ·
1561 AGTCGTGGCCGCTGCCTGTGTCCTCATCTTGGCTCTCTTCCTTGTCCACCGGCGAAAGAA
      · E   T   R   Y   G   E   V   F   E   P   T   V   E   R   G   E   L   V   V   R ·
1621 GGAGACCCGTTATGGAGAAGTGTTTGAACCAACAGTGGAAAGAGGTGAACTGGTAGTCAG
      · Y   R   V   R   K   S   Y   S   R   R   T   T   E   A   T   L   N   S   L   G ·
1681 GTACCGCGTGCGCAAGTCCTACAGTCGTCGGACCACTGAAGCTACCTTGAACAGCCTGGG
      · I   S   E   E   L   K   E   K   L   R   D   V   M   V   D   R   H   K   V   A ·
1741 CATCAGTGAAGAGCTGAAGGAGAAGCTGCGGGATGTGATGGTGGACCGGCACAAGGTGGC
      · L   G   K   T   L   G   E   G   E   F   G   A   V   M   E   G   Q   L   N   Q ·
1801 CCTGGGGAAGACTCTGGGAGAGGGAGAGTTTGGAGCTGTGATGGAAGGCCAGCTCAACCA
      · D   D   S   I   L   K   V   A   V   K   T   M   K   I   A   I   C   T   R   S ·
1861 GGACGACTCCATCCTCAAGGTGGCTGTGAAGACGATGAAGATTGCCATCTGCACGAGGTC
      · E   L   E   D   F   L   S   E   A   V   C   M   K   E   F   D   H   P   N   V ·
1921 AGAGCTGGAGGATTTCCTGAGTGAAGCGGTCTGCATGAAGGAATTTGACCATCCCAACGT
      · M   R   L   I   G   V   C   F   Q   G   S   E   R   E   S   F   P   A   P   V ·
1981 CATGAGGCTCATCGGTGTCTGTTTCCAGGGTTCTGAACGAGAGAGCTTCCCAGCACCTGT
      · V   I   L   P   F   M   K   H   G   D   L   H   S   F   L   L   Y   S   R   L ·
2041 GGTCATCTTACCTTTCATGAAACATGGAGACCTACACAGCTTCCTCCTCTATTCCCGGCT
      · G   D   Q   P   V   Y   L   P   T   Q   M   L   V   K   F   M   A   D   I   A ·
2101 CGGGGACCAGCCAGTGTACCTGCCCACTCAGATGCTAGTGAAGTTCATGGCAGACATCGC
      · S   G   M   E   Y   L   S   T   K   R   F   I   H   R   D   L   A   A   R   N ·
2161 CAGTGGCATGGAGTATCTGAGTACCAAGAGATTCATACACCGGGACCTGGCGGCCAGGAA
      · C   M   L   N   E   N   M   S   V   C   V   A   D   F   G   L   S   K   K   I ·
2221 CTGCATGCTGAATGAGAACATGTCCGTGTGTGTGGCGGACTTCGGGCTCTCCAAGAAGAT
      · Y   N   G   D   Y   Y   R   Q   G   R   I   A   K   M   P   V   K   W   I   A ·
2281 CTACAATGGGGACTACTACCGCCAGGGACGTATCGCCAAGATGCCAGTCAAGTGGATTGC
      · I   E   S   L   A   D   R   V   Y   T   S   K   S   D   V   W   S   F   G   V ·
2341 CATTGAGAGTCTAGCTGACCGTGTCTACACCAGCAAGAGCGATGTGTGGTCCTTCGGGGT
      · T   M   W   E   I   A   T   R   G   Q   T   P   Y   P   G   V   E   N   S   E ·
2401 GACAATGTGGGAGATTGCCACAAGAGGCCAAACCCCATATCCGGGCGTGGAGAACAGCGA
      · I   Y   D   Y   L   R   Q   G   N   R   L   K   Q   P   A   D   C   L   D   G ·
2461 GATTTATGACTATCTGCGCCAGGGAAATCGCCTGAAGCAGCCTGCGGACTGTCTGGATGG
      · L   Y   A   L   M   S   R   C   W   E   L   N   P   Q   D   R   P   S   F   T ·
2521 ACTGTATGCCTTGATGTCGCGGTGCTGGGAGCTAAATCCCCAGGACCGGCCAAGTTTTAC
      · E   L   R   E   D   L   E   N   T   L   K   A   L   P   P   A   Q   E   P   D ·
2581 AGAGCTGCGGGAAGATTTGGAGAACACACTGAAGGCCTTGCCTCCTGCCCAGGAGCCTGA
      · E   I   L   Y   V   N   M   D   E   G   G   Y   P   E   P   P   G   A   A ·
2641 CGAAATCCTCTATGTCAACATGGATGAGGGTGGAGGTTATCCTGAACCCCCTGGAGCTGC
      · G   G   A   D   P   P   T   Q   P   D   P   K   D   S   C   S   C   L   T   A ·
```

Fig. 1 (continued)

```
2701 AGGAGGAGCTGACCCCCCAACCCAGCCAGACCCTAAGGATTCCTGTAGCTGCCTCACTGC
      · A  E  V  H  P  A  G  R  Y  V  L  C  P  S  T  T  P  S  P  A ·
2761 GGCTGAGGTCCATCCTGCTGGACGCTATGTCCTCTGCCCTTCCACAACCCCTAGCCCCGC
      · Q  P  A  D  R  G  S  P  A  A  P  G  Q  E  D  G  A  *
2821 TCAGCCTGCTGATAGGGGCTCCCCAGCAGCCCCAGGGCAGGAGGATGGTGCCTGAGACAA
2881 CCCTCCACCTGGTACTCCCTCTCAGGATCCAAGCTAAGCACTGCCACTGGGGAAAACTCC
2941 ACCTTCCCACTTTCCCACCCCACGCCTTATCCCCACTTGCAGCCCTGTCTTCCTACCTAT
3001 CCCACCTCCATCCCAGACAGGTCCCTCCCCTTCTCTGTGCAGTAGCATCACCTTGAAAGC
3061 AGTAGCATCACCATCTGTAAAGGAAGGGGTTGGATTGCAATATCTGAAGCCCTCCCAGG
3121 TGTTAACATTCCAAGACTCTAGAGTCCAAGGTTTAAAGAGTCTAGATTCAAAGGTTCTAG
3181 GTTTCAAAGATGCTGTGAGTCTTTGGTTCTAAGGACCTGAAATTCCAAAGTCTCTAATTC
3241 TATTAAAGTGCTAAGGTTCTAAGGCCTACTTTTTTTTTTTTTTTTTTTTTTTTTTT
3301 GCGATAGAGTCTCACTGTGTCACCCAGGCTGGAGTGCAGTGGTGCAATCTCGCCTCACTG
3361 CAACCTTCACCTACCGAGTTCAAGTGATTTTCCTGCCTTGGCCTCCCAAGTAGCTGGGAT
3421 TACAGGTGTGTGCCACCACACCCGGCTAATTTTTATATTTTTAGTAGAGACAGGGTTTCA
3481 CCATGTTGGCCAGGCTGGTCTAAAACTCCTGACCTCAAGTGATCTGCCCACCTCAGCCTC
3541 CCAAAGTGCTGAGATTACAGGCATGAGCCACTGCACTCAACCTTAAGACCTACTGTTCTA
3601 AAGCTCTGACATTATGTGGTTTTAGATTTTCTGGTTCTAACATTTTTGATAAAGCCTCAA
3661 GGTTTTAGGTTCTAAAGTTCTAAGATTCTGATTTTAGGAGCTAAGGCTCTATGAGTCTAG
3721 ATGTTTATTCTTCTAGAGTTCAGAGTCCTTAAAATGTAAGATTATAGATTCTAAAGATTC
3781 TATAGTTCTAGACATGGAGGTTCTAAGGCCTAGGATTCTAAAATGTGATGTTCTAAGGCT
3841 CTGAGAGTCTAGATTCTCTGGCTGTAAGGCTCTAGATCATAAGGCTTCAAAATGTTATCT
3901 TCTCAAGTTCTAAGATTCTAATGATGATCAATTATAGTTTCTGAGGCTTTATGATAATAG
3961 ATTCTTGTATAAGATCCTAGATCCTAAGGGTCGAAAGCTCTAGAATCTGCAATTCAAA
4021 AGTTCCAAGAGTCTAAAGATGGAGTTTCTAAGGTCCGGTGTTCTAAGATGTGATATTCTA
4081 AGACTTACTCTAAGATCTTAGATTCTCTGTGTCTAAGATTCTAGATCAGATGCTCCAAGA
4141 TTCTAGATGATTAAATAAGATTCTAACGGTCTGTTCTGTTTCAAGGCACTCTAGATTCCA
4201 TTGGTCCAAGATTCCGGATCCTAAGCATCTAAGTTATAAGACTCTCACACTCAGTTGTGA
4261 CTAACTAGACACCAAAGTTCTAATAATTTCTAATGTTGGACACCTTTAGGTTCTTTGCTG
4321 CATTCTGCCTCTCTAGGACCATGGTTAAGAGTCCAAGAATCCACATTTCTAAAATCTTAT
4381 AGTTCTAGGCACTGTAGTTCTAAGACTCAAATGTTCTAAGTTTCTAAGATTCTAAAGGTC
4441 CACAGGTCTAGACTATTAGGTGCAATTTCAAGGTTCTAACCCTATACTGTAGTATTCTTT
4501 GGGGTGCCCCTCTCCTTCTTAGCTATCATTGCTTCCTCCTCCCAACTGTGGGGTGTGC
4561 CCCCTTCAAGCCTGTGCAATGCATTAGGGATGCCTCCTTTCCGCAGGGGATGGACGATC
4621 TCCCACCTTTCGGGCCATGTTGCCCCGTGAGCCAATCCCTCACCTTCTGAGTACAGAGT
4681 GTGGACTCTGGTGCCTCCAGAGGGGCTCAGGTCACATAAAACTTTGTATATCAACGAAAA
4741 AAA
```

Fig. 2A

```
         Q   L   Q   L   Q   E   S   G   P   G   L   V   R   P   S   E   T   L   S   L
   1  CAGCTGCAGCTGCAGGAGTCGGGCCCAGGACTGGTGAGGCCTTCGGAGACCCTGTCCCTC
         T   C   T   V   S   G   V   S   I   T   N   S   S   Y   H   W   G   W   I   R
  61  ACCTGCACTGTCTCTGGTGTCTCCATCACCAATAGCAGTTACCACTGGGGCTGGATCCGC
         Q   P   P   G   K   G   L   E   W   I   G   S   I   F   Y   N   G   N   T   F
 121  CAGCCCCCAGGGAAGGGGCTGGAGTGGATTGGGAGTATCTTTTATAATGGGAACACCTTC
         F   N   P   S   L   K   S   R   V   T   L   S   V   D   T   S   K   N   Q   F
 181  TTCAACCCGTCCCTCAAGAGTCGAGTCACCTTATCCGTCGACACGTCCAAGAACCAATTC
         S   L   K   L   S   P   V   T   A   A   D   T   A   V   Y   Y   C   E   R   Q
 241  TCCCTGAAACTGAGTCCTGTGACCGCCGCAGACACGGCTGTGTATTACTGTGAGAGACAG
         D   N   W   N   F   R   H   Y   F   N   Y   W   G   Q   G   T   L   V   T   V
 301  GATAACTGGAACTTCCGGCACTACTTTAACTATTGGGGCCAGGGAACCCTGGTCACCGTC
         S   S   A   K   T   T   P   P   S   V   Y   P   L   A   P   G   S   A   A   Q
 361  TCCTCAGCCAAAACGACACCCCCATCTGTCTATCCACTGGCCCCTGGATCTGCTGCCCAA
         T   N   S   M   V   T   L   G   C   L   V   K   G   Y   F   P   E   P   V   T
 421  ACTAACTCCATGGTGACCCTGGGATGCCTGGTCAAGGGCTATTTCCCTGAGCCAGTGACA
         V   T   W   N   S   G   S   L   S   S   G   V   H   T   F   P   A   V   L   Q
 481  GTGACCTGGAACTCTGGATCCCTGTCCAGCGGTGTGCACACCTTCCCAGCTGTCCTGCAG
         S   D   L   Y   T   L   S   S   S   V   T   V   P   S   S   T   W   P   S   E
 541  TCTGACCTCTACACTCTGAGCAGCTCAGTGACTGTCCCCTCCAGCACCTGGCCCAGCGAG
         T   V   T   C   N   V   A   H   P   A   S   S   T   K   V   D   K   K   I   V
 601  ACCGTCACCTGCAACGTTGCCCACCCGGCCAGCAGCACCAAGGTGGACAAGAAAATTGTG
         P   R   D   C   G   C   K   P   C   I   C   T   V   P   E   V   S   S   V   F
 661  CCCAGGGATTGTGGTTGTAAGCCTTGCATATGTACAGTCCCAGAAGTATCATCTGTCTTC
         I   F   P   P   K   P   K   D   V   L   T   I   T   L   T   P   K   V   T   C
 721  ATCTTCCCCCCAAAGCCCAAGGATGTGCTCACCATTACTCTGACTCCTAAGGTCACGTGT
         V   V   V   D   I   S   K   D   D   P   E   V   Q   F   S   W   F   V   D   D
 781  GTTGTGGTAGACATCAGCAAGGATGATCCCGAGGTCCAGTTCAGCTGGTTTGTAGATGAT
         V   E   V   H   T   A   Q   T   Q   P   R   E   E   Q   F   N   S   T   F   R
 841  GTGGAGGTGCACACAGCTCAGACGCAACCCCGGGAGGAGCAGTTCAACAGCACTTTCCGC
         S   V   S   E   L   P   I   M   H   Q   D   W   L   N   G   K   E   F   K   C
 901  TCAGTCAGTGAACTTCCCATCATGCACCAGGACTGGCTCAATGGCAAGGAGTTCAAATGC
         R   V   N   S   A   A   F   P   A   P   I   E   K   T   I   S   K   T   K   G
 961  AGGGTCAACAGTGCAGCTTTCCCTGCCCCCATCGAGAAAACCATCTCCAAAACCAAAGGC
         R   P   K   A   P   Q   V   Y   T   I   P   P   P   K   E   Q   M   A   K   D
1021  AGACCGAAGGCTCCACAGGTGTACACCATTCCACCTCCCAAGGAGCAGATGGCCAAGGAT
         K   V   S   L   T   C   M   I   T   D   F   F   P   E   D   I   T   V   E   W
1081  AAAGTCAGTCTGACCTGCATGATAACAGACTTCTTCCCTGAAGACATTACTGTGGAGTGG
         Q   W   N   G   Q   P   A   E   N   Y   K   N   T   Q   P   I   M   D   T   D
1141  CAGTGGAATGGGCAGCCAGCGGAGAACTACAAGAACACTCAGCCCATCATGGACACAGAT
```

Fig. 2A (continued)

```
             G   S   Y   F   V   Y   S   K   L   N   V   Q   K   S   N   W   E   A   G   N
1201    GGCTCTTACTTCGTCTACAGCAAGCTCAATGTGCAGAAGAGCAACTGGGAGGCAGGAAAT
         T   F   T   C   S   V   L   H   E   G   L   H   N   H   H   T   E   K   S   L
1261    ACTTTCACCTGCTCTGTGTTACATGAGGGTCTGCACAACCACCATACTGAGAAGAGCCTC
         S   H   S   P   G   K
1321    TCCCACTCTCCTGGTAAA
```

Fig. 2B

```
             D   I   Q   M   T   Q   S   P   S   T   L   S   A   S   V   G   D   R   V   T
1       GACATCCAGATGACCCAGTCTCCTTCCACCCTGTCTGCATCTGTCGGAGACAGAGTCACC
         I   T   C   R   A   S   Q   S   I   S   N   W   L   A   W   Y   Q   Q   K   P
61      ATCACTTGCCGGGCCAGTCAGAGTATTAGTAACTGGTTGGCCTGGTATCAGCAGAAACCA
         G   K   A   P   K   L   L   I   Y   K   A   S   S   L   E   S   G   V   P   S
121     GGGAAAGCCCCTAAACTCCTGATCTATAAGGCGTCTAGTTTAGAAAGTGGGGTCCCATCA
         R   F   S   G   S   G   S   G   T   E   F   T   L   T   I   S   S   L   Q   P
181     AGGTTCAGCGGCAGTGGATCTGGGACAGAGTTCACTCTCACCATCAGCAGCCTGCAGCCT
         D   D   F   A   T   Y   Y   C   Q   Q   Y   N   S   Y   Y   T   F   G   Q   G
241     GATGATTTTGCTACTTATTACTGCCAACAGTATAATAGTTATTACACTTTTGGCCAGGGG
         T   K   L   E   I   K   R   A   D   A   A   P   T   V   S   I   F   P   P   S
301     ACCAAGCTGGAGATCAAGCGGGCTGATGCTGCACCAACTGTATCCATCTTCCCACCATCC
         S   E   Q   L   T   S   G   G   A   S   V   V   C   F   L   N   N   F   Y   P
361     AGTGAGCAGTTAACATCTGGAGGTGCCTCAGTCGTGTGCTTCTTGAACAACTTCTACCCC
         K   D   I   N   V   K   W   K   I   D   G   S   E   R   Q   N   G   V   L   N
421     AAAGACATCAATGTCAAGTGGAAGATTGATGGCAGTGAACGACAAAATGGCGTCCTGAAC
         S   W   T   D   Q   D   S   K   D   S   T   Y   S   M   S   S   T   L   T   L
481     AGTTGGACTGATCAGGACAGCAAAGACAGCACCTACAGCATGAGCAGCACCCTCACGTTG
         T   K   D   E   Y   E   R   H   N   S   Y   T   C   E   A   T   H   K   T   S
541     ACCAAGGACGAGTATGAACGACATAACAGCTATACCTGTGAGGCCACTCACAAGACATCA
         T   S   P   I   V   K   S   F   N   R   N   E   C
601     ACTTCACCCATTGTCAAGAGCTTCAACAGGAATGAGTGT
```

Fig. 3A

```
  1   QLQLQESGPGLVRPSETLSLTCTVSGVSITNSSYHWGWIRQPPGKGLEWI
 51   GSIFYNGNTFFNPSLKSRVTLSVDTSKNQFSLKLSPVTAADTAVYYCERQ
101   DNWNFRHYFNYWGQGTLVTVSSAKTTPPSVYPLAPGSAAQTNSMVTLGCL
151   VKGYFPEPVTVTWNSGSLSSGVHTFPAVLQSDLYTLSSSVTVPSSTWPSE
201   TVTCNVAHPASSTKVDKKIVPRDCGCKPCICTVPEVSSVFIFPPKPKDVL
251   TITLTPKVTCVVVDISKDDPEVQFSWFVDDVEVHTAQTQPREEQFNSTFR
301   SVSELPIMHQDWLNGKEFKCRVNSAAFPAPIEKTISKTKGRPKAPQVYTI
351   PPPKEQMAKDKVSLTCMITDFFPEDITVEWQWNGQPAENYKNTQPIMDTD
401   GSYFVYSKLNVQKSNWEAGNTFTCSVLHEGLHNHHTEKSLSHSPGK
```

Fig. 3B

```
  1   DIQMTQSPSTLSASVGDRVTITCRASQSISNWLAWYQQKPGKAPKLLIYK
 51   ASSLESGVPSRFSGSGSGTEFTLTISSLQPDDFATYYCQQYNSYYTFGQG
101   TKLEIKRADAAPTVSIFPPSSEQLTSGGASVVCFLNNFYPKDINVKWKID
151   GSERQNGVLNSWTDQDSKDSTYSMSSTLTLTKDEYERHNSYTCEATHKTS
201   TSPIVKSFNRNEC
```

Fig. 4A

```
                                           <------------------------------FR1-IMGT------------------------------>
                                            Q  L  Q  L  Q  E  S  G  P  G  L  V  R  P  S  E  T  L  S  L  T  C  T  V  S  G  V  S  I  T
V  94.0% (281/299)  2a37         1  CAGCTGCAGCTGCAGGAGTCGCAGGAGTCGGGCCCAGGACTGGTGAGGCCTTCGGAGACTCCACCTGCACTGTCTCCATCACC  90
                    IGHV4-39*01  1  ..........................................A..............K..........G.....S       90

<--------CDR1--------><-------------FR2-------------><--------CDR2--------
                                            N  S  S  Y  H  W  G   W  I  R  Q  P  P  G  K  G  L  E  W  I  G  S  I  F  Y  N  G  N  T  F
V  94.0% (281/299)  2a37         91 AATAGCAGTTACCACTGGGGCTGGATCCGCCAGCCCCCAGGGAAGGGGCTGGAGTGGATTGGGAGTATCTTTTATAATGGGAACACCTTC 180
                    IGHV4-39*01  91 .G....T.....T..........................................A.....G.....G.....A           180
                                            S  S  S  Y           Y                                  Y  Y  S  S     T     Y

-------><---------------FR3---------------
                                            F  N  P  S  L  K  S  R  V  T  L  S  V  D  T  S  K  N  Q  F  S  L  K  L  S  P  V  T  A  A
V  94.0% (281/299)  2a37        181 TTCAACCCGTCCCTCAAGAGTCGAGTCACCTTATCGTCGACACGTCCAAGAACCAATTCTCCCTGAAACTGAGTCCTGTGACCGCCGCA 270
                    IGHV4-39*01 181 .A....................................A..........G..........G.......CT               270
                                            Y  N  P  S  L  K  S  R  V  T  I  S  V  D  T  S  K  N  Q  F  S  L  K  L  S     V  T  A  A

><--------CDR3--------><----FR4---->
                                            D  T  A  V  Y  Y  C  E  R  Q  D  N  W  N  F  R  H  Y  F  N  Y  W  G  Q  G  T  L  V  T  V
V  94.0% (281/299)  2a37        271 GACACGGCTGTGTATTACTGTGAGAGACAGGATAACTGGAACTTCCGGCACTACTTTAACTATTGGGGCCAGGGAACCCTGGTCACCGTC 360
                    IGHV4-39*01 271 ...............C.......                                  .............G....C.....A        299
                                            D  T  A  V  Y  Y  C  A  R

D  100.0% (12/12)   IGHD1-7*01   4                                                                                         15
J  93.6% (44/47)    IGHJ4*01     1                                                                                         41

------>
                                            S  S
J  95.7% (45/47)    2a37        361 TCCTCA 366
                    IGHJ4*02    42  ...... 47
```

Fig. 4B

```
                            <-------------------------FR1--------------------------><----CDR1----
                            D  I  Q  M  T  Q  S  P  S  T  L  S  A  S  V  G  D  R  V  T  I  T  C  R  A  S  Q  S  I  S
V 98.2% (278/283)  2a37   1 GACATCCAGATGACCCAGTCTCCTTCCACCCTGTCTGCATCTGTCGGAGACAGAGTCACCATCACTTGCCGGGCCAGTCAGAGTATTAGT 90
                   IGKV1-5*03 1 ....................................................A................................ 90
                                                                                                D  I  Q  M  T  Q  S  P  S  T  L  S  A  S  V  G  D  R  V  T  I  T  C  R  A  S  Q  S  I  S

><-------FR2--------><----CDR2---->
                            N  W  L  A  W  Y  Q  Q  K  P  G  K  A  P  K  L  L  I  Y  K  A  S  S  L  E  S  G  V  P  S
V 98.2% (278/283)  2a37  91 AACTGGTTGGCCTGGTATCAGCAGAAACCAGGGAAAGCCCCTAAACTCCTGATCTATAAGGCGTCTAGTTTAGAAAGTGGGGTCCCATCA 180
                   IGKV1-5*03 91 .G.......S........................................G................................... 180
                                 S  W  L  A  W  Y  Q  Q  K  P  G  K  A  P  K  L  L  I  Y  K  A  S  S  L  E  S  G  V  P  S

<-------------------FR3-------------------------------><
                            R  F  S  G  S  G  S  G  T  E  F  T  L  T  I  S  S  L  Q  P  D  D  F  A  T  Y  Y  C  Q  Q
V 98.2% (278/283)  2a37 181 AGGTTCAGCGGCAGTGGATCTGGGACAGAGTTCACTCTCACCATCAGCAGCCTGCAGCCTGATGATTTTGCTACTTATTACTGCCAACAG 270
                   IGKV1-5*03 181 ...............................................A..................................... 270
                                 R  F  S  G  S  G  S  G  T  E  F  T  L  T  I  S  S  L  Q  P  D  D  F  A  T  Y  Y  C  Q  Q

----CDR3----><------FR4------>
                            Y  N  S  Y  Y  T  F  G  Q  G  T  K  L  E  I  K  R
V 98.2% (278/283)  2a37 271 TATAATAGTTATTACACTTTTGGCCAGGGGACCAAGCTGGAGATCAAGCGG 321
                   IGKV1-5*03 271 .................. 287
                                 Y  N  S  Y
```

Fig. 6A(i)
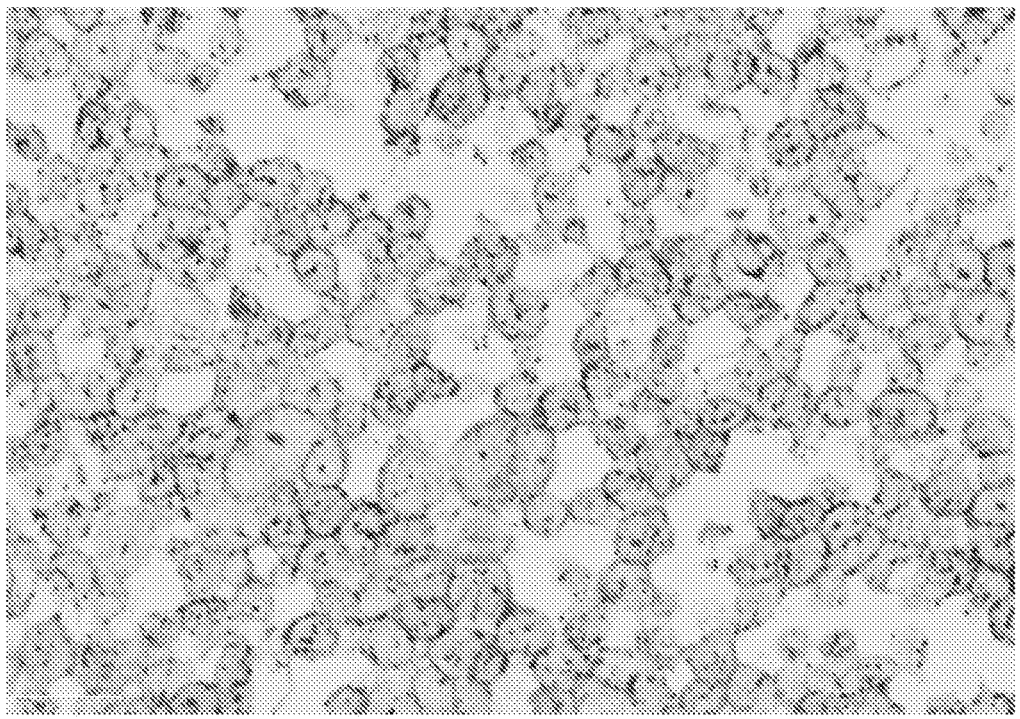
Fig. 6A(ii)
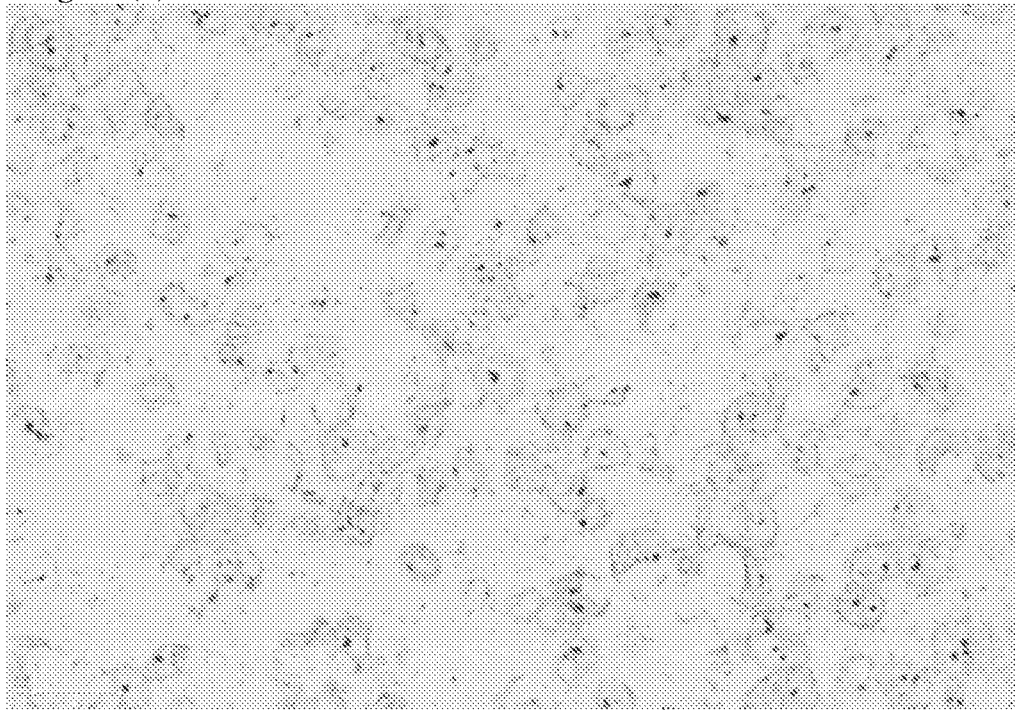

Fig. 6A(iii)
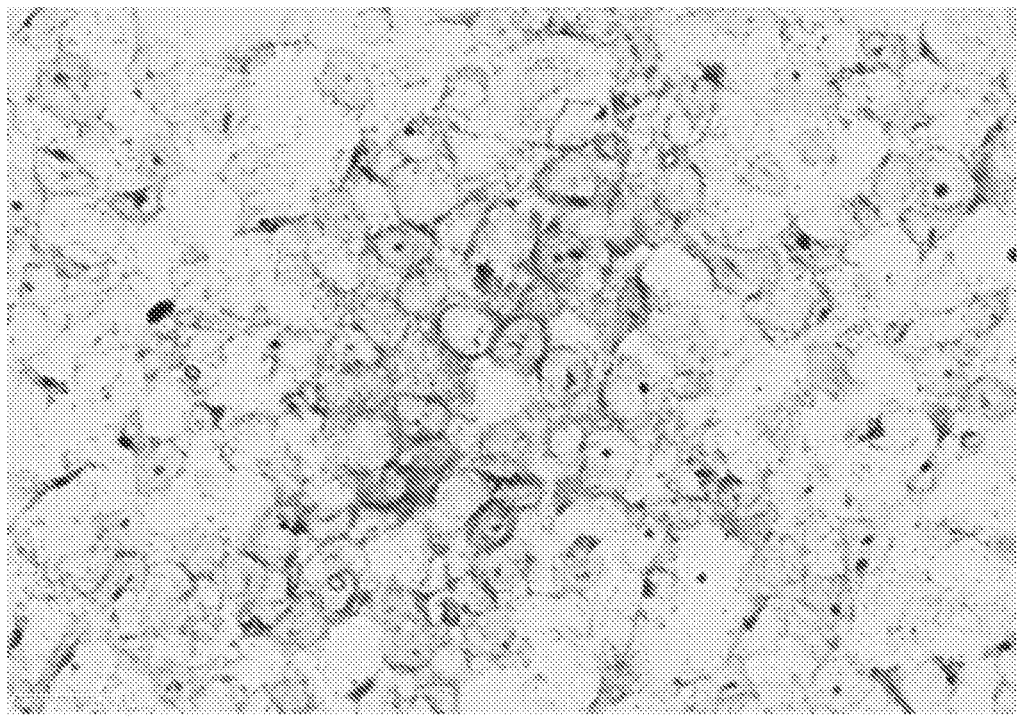

Fig. 6B(i)
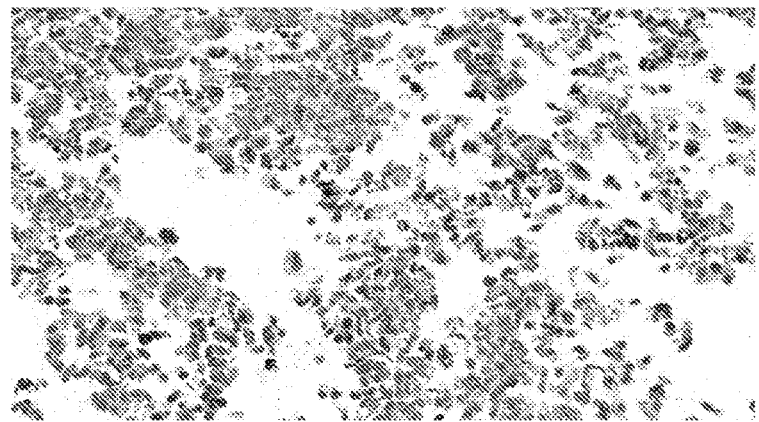
Fig. 6B(ii)
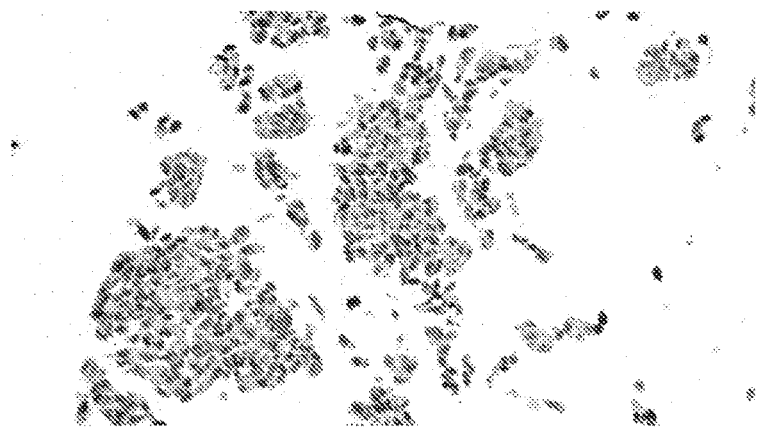
Fig. 6B(iii)
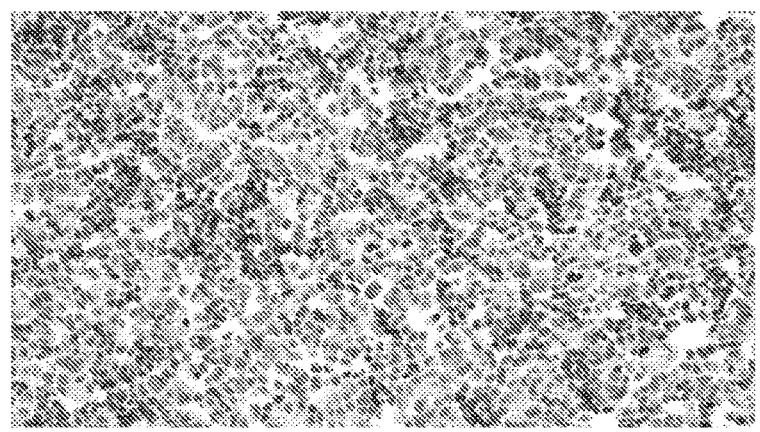

Fig. 6B(iv)
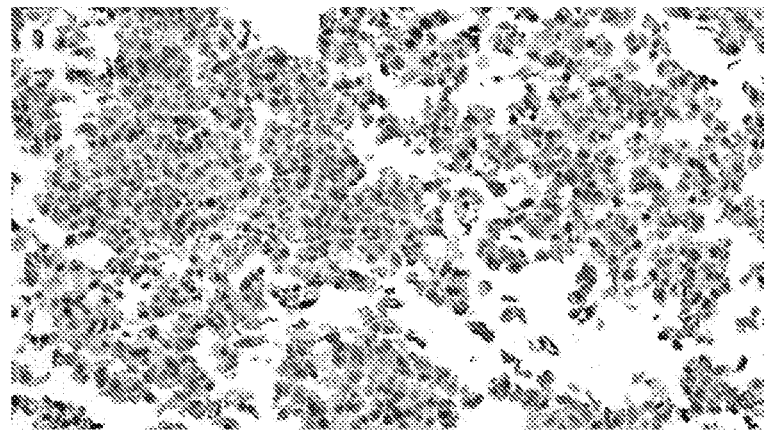
Fig. 6B(v)
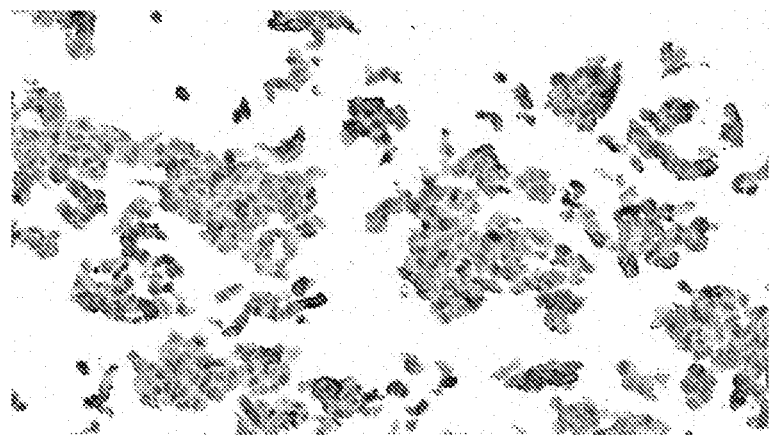
Fig. 6B(vi)
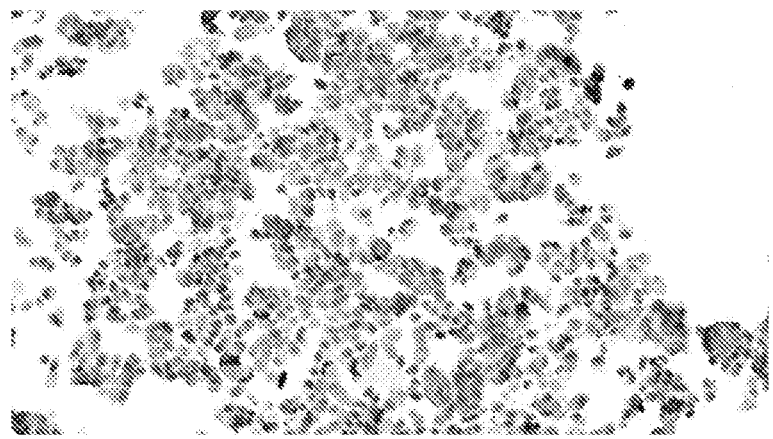

SEQUENCE LISTING

<160> NUMBER OF SEQ ID NOS: 31

<210> SEQ ID NO 1
<211> LENGTH: 4743
<212> TYPE: DNA
<213> ORGANISM: Homo sapiens

<400> SEQUENCE: 1

```
gggaaggagg caggggtgct gagaaggcgg ctgctgggca gagccggtgg caagggcctc      60
ccctgccgct gtgccaggca ggcagtgcca atccgggga gcctggagct gggggagggg     120
ccggggacag cccggccctg cccctcccc cgctgggagc ccaacaactt ctgaggaaag     180
tttggcaccc atggcgtggc ggtgcccag gatgggcagg gtcccgctgg cctggtgctt     240
ggcgctgtgc ggctgggcgt gcatggcccc caggggcacg caggctgaag aaagtcccct     300
```

```
cgtgggcaac ccagggaata tcacaggtgc ccggggactc acgggcaccc ttcggtgtca    360
gctccaggtt cagggagagc cccccgaggt acattggctt cgggatggac agatcctgga    420
gctcgcggac agcacccaga cccaggtgcc cctgggtgag gatgaacagg atgactggat    480
agtggtcagc cagctcagaa tcacctccct gcagctttcc gacacgggac agtaccagtg    540
tttggtgttt ctgggacatc agaccttcgt gtcccagcct ggctatgttg ggctggaggg    600
cttgccttac ttcctggagg agcccgaaga caggactgtg gccgccaaca ccccttcaa    660 cctgagctgc caagctcagg gaccccaga gcccgtggac ctactctggc tccaggatgc    720 tgtcccctg gccacggctc caggtcacgg ccccagcgc agcctgcatg ttccagggct    780
gaacaagaca tcctctttct cctgcgaagc ccataacgcc aaggggtca ccacatcccg    840 cacagccacc atcacagtgc tcccccagca gcccgtaac ctccacctgg tctcccgcca    900
acccacggag ctggaggtgg cttggactcc aggcctgagc ggcatctacc ccctgaccca    960
ctgcaccctg caggctgtgc tgtcagacga tgggatgggc atccaggcgg gagaaccaga   1020
ccccccagag gagcccctca cctcgcaagc atccgtgccc cccatcagc ttcggctagg   1080 cagcctccat cctcacaccc cttatcacat ccgcgtggca tgcaccagca gccagggccc   1140
ctcatcctgg acccactggc ttcctgtgga gacgccggag ggagtgcccc tgggcccccc   1200
tgagaacatt agtgctacgc ggaatgggag ccaggccttc gtgcattggc aagagccccg   1260
ggcgcccctg cagggtaccc tgttagggta ccggctggcg tatcaaggcc aggacacccc   1320
agaggtgcta atggacatag ggctaaggca agaggtgacc ctggagctgc agggggacgg   1380
gtctgtgtcc aatctgacag tgtgtgtggc agcctacact gctgctgggg atggaccctg   1440
gagcctccca gtaccctgg aggcctggcg cccagggcaa gcacagccag tccaccagct   1500
ggtgaaggaa ccttcaactc ctgccttctc gtgccctgg tggtatgtac tgctaggagc   1560
agtcgtggcc gctgcctgtg tcctcatctt ggctctcttc cttgtccacc ggcgaaagaa   1620
ggagacccgt tatggagaag tgtttgaacc aacagtggaa agaggtgaac tggtagtcag   1680
gtaccgcgtg cgcaagtcct acagtcgtcg gaccactgaa gctaccttga acagcctggg   1740
catcagtgaa gagctgaagg agaagctgcg ggatgtgatg gtggaccggc acaaggtggc   1800
cctggggaag actctgggag agggagagtt tggagctgtg atggaaggcc agctcaacca   1860
ggacgactcc atcctcaagg tggctgtgaa gacgatgaag attgccatct gcacgaggtc   1920
agagctggag gatttcctga gtgaagcggt ctgcatgaag gaatttgacc atccaacgt   1980 catgaggctc atcggtgtct gtttccaggg ttctgaacga gagagcttcc cagcacctgt   2040
ggtcatctta ccttttcatga aacatggaga cctacacagc ttcctcctct attcccggct   2100
cggggaccag ccagtgtacc tgcccactca gatgctagtg aagttcatgg cagacatcgc   2160
cagtggcatg gagtatctga gtaccaagag attcatacac cgggacctgg cggccaggaa   2220
ctgcatgctg aatgagaaca tgtccgtgtg tgtggcggac ttcgggctct ccaagaagat   2280
ctacaatggg gactactacc gccagggacg tatcgccaag atgccagtca agtggattgc   2340
cattgagagt ctagctgacc gtgtctacac cagcaagagc gatgtgtggt ccttcggggt   2400
gacaatgtgg gagattgcca aagaggcca aaccccatat ccgggcgtgg agaacagcga   2460 gattatgac tatctgcgcc agggaaatcg cctgaagcag cctgcggact gtctggatgg   2520
actgtatgcc ttgatgtcgc ggtgctggga gctaaatccc caggaccggc caagttttac   2580
agagctgcgg gaagatttgg agaacacact gaaggccttg cctcctgccc aggagcctga   2640
cgaaatcctc tatgtcaaca tggatgaggg tggaggttat cctgaacccc ctggagctgc   2700
```

```
aggaggagct gaccccccaa cccagccaga ccctaaggat tcctgtagct gcctcactgc    2760
ggctgaggtc catcctgctg gacgctatgt cctctgccct tccacaaccc ctagccccgc    2820
tcagcctgct gatagggggct ccccagcagc cccagggcag gaggatggtg cctgagacaa   2880
ccctccacct ggtactccct ctcaggatcc aagctaagca ctgccactgg ggaaaactcc    2940
accttcccac tttcccaccc cacgccttat ccccacttgc agccctgtct tcctacctat    3000
cccacctcca tcccagacag gtccctcccc ttctctgtgc agtagcatca ccttgaaagc    3060
agtagcatca ccatctgtaa aaggaagggg ttggattgca atatctgaag ccctcccagg    3120
tgttaacatt ccaagactct agagtccaag gtttaaagag tctagattca aaggttctag    3180
gtttcaaaga tgctgtgagt ctttggttct aaggacctga aattccaaag tctctaattc    3240
tattaaagtg ctaaggttct aaggcctact ttttttttt ttttttttt ttttttttt      3300 gcgatagagt ctcactgtgt cacccaggct ggagtgcagt ggtgcaatct cgcctcactg    3360
caaccttcac ctaccgagtt caagtgattt tcctgccttg gcctcccaag tagctgggat    3420
tacaggtgtg tgccaccaca cccggctaat ttttatattt ttagtagaga cagggtttca    3480
ccatgttggc caggctggtc taaaactcct gacctcaagt gatctgccca cctcagcctc    3540
ccaaagtgct gagattacag gcatgagcca ctgcactcaa ccttaagacc tactgttcta    3600
aagctctgac attatgtggt tttagatttt ctggttctaa cattttgat aaagcctcaa     3660 ggttttaggt tctaaagttc taagattctg attttaggag ctaaggctct atgagtctag    3720
atgtttattc ttctagagtt cagagtcctt aaaatgtaag attatagatt ctaaagattc    3780
tatagttcta gacatggagg ttctaaggcc taggattcta aaatgtgatg ttctaaggct    3840
ctgagagtct agattctctg gctgtaaggc tctagatcat aaggcttcaa atgttatct    3900 tctcaagttc taagattcta atgatgatca attatagttt ctgaggcttt atgataatag    3960
attctcttgt ataagatcct agatcctaag ggtcgaaagc tctagaatct gcaattcaaa    4020
agttccaaga gtctaaagat ggagtttcta aggtccggtg ttctaagatg tgatattcta    4080
agacttactc taagatctta gattctctgt gtctaagatt ctagatcaga tgctccaaga    4140
ttctagatga ttaaataaga ttctaacggt ctgttctgtt tcaaggcact ctagattcca    4200
ttggtccaag attccggatc ctaagcatct aagttataag actctcacac tcagttgtga    4260
ctaactagac accaaagttc taataatttc taatgttgga caccttagg ttctttgctg     4320 cattctgcct ctctaggacc atggttaaga gtccaagaat ccacatttct aaaatcttat    4380
agttctaggc actgtagttc taagactcaa atgttctaag tttctaagat tctaaaggtc    4440
cacaggtcta gactattagg tgcaatttca aggttctaac cctatactgt agtattcttt    4500
ggggtgcccc tctccttctt agctatcatt gcttcctcct ccccaactgt ggggggtgtgc   4560 cccctccaag cctgtgcaat gcattaggga tgcctccttt cccgcagggg atggacgatc   4620 tcccacctt cgggccatgt tgcccccgtg agccaatccc tcaccttctg agtacagagt     4680
gtggactctg gtgcctccag aggggctcag gtcacataaa actttgtata tcaacgaaaa    4740
aaa                                                                  4743
```

<210> SEQ ID NO 2
<211> LENGTH: 894
<212> TYPE: PRT
<213> ORGANISM: Homo sapiens

<400> SEQUENCE: 2

-continued

```
Met Ala Trp Arg Cys Pro Arg Met Gly Arg Val Pro Leu Ala Trp Cys
1               5                   10                  15
Leu Ala Leu Cys Gly Trp Ala Cys Met Ala Pro Arg Gly Thr Gln Ala
            20                  25                  30
Glu Glu Ser Pro Phe Val Gly Asn Pro Gly Asn Ile Thr Gly Ala Arg
        35                  40                  45
Gly Leu Thr Gly Thr Leu Arg Cys Gln Leu Gln Val Gln Gly Glu Pro
    50                  55                  60
Pro Glu Val His Trp Leu Arg Asp Gly Gln Ile Leu Glu Leu Ala Asp
65                  70                  75                  80
Ser Thr Gln Thr Gln Val Pro Leu Gly Glu Asp Glu Gln Asp Asp Trp
                85                  90                  95
Ile Val Val Ser Gln Leu Arg Ile Thr Ser Leu Gln Leu Ser Asp Thr
                100                 105                 110
Gly Gln Tyr Gln Cys Leu Val Phe Leu Gly His Gln Thr Phe Val Ser
            115                 120                 125
Gln Pro Gly Tyr Val Gly Leu Glu Gly Leu Pro Tyr Phe Leu Glu Glu
        130                 135                 140
Pro Glu Asp Arg Thr Val Ala Ala Asn Thr Pro Phe Asn Leu Ser Cys
145                 150                 155                 160
Gln Ala Gln Gly Pro Pro Glu Pro Val Asp Leu Leu Trp Leu Gln Asp
                165                 170                 175
Ala Val Pro Leu Ala Thr Ala Pro Gly His Gly Pro Gln Arg Ser Leu
                180                 185                 190
His Val Pro Gly Leu Asn Lys Thr Ser Ser Phe Ser Cys Glu Ala His
            195                 200                 205
Asn Ala Lys Gly Val Thr Thr Ser Arg Thr Ala Thr Ile Thr Val Leu
210                 215                 220
Pro Gln Gln Pro Arg Asn Leu His Leu Val Ser Arg Gln Pro Thr Glu
225                 230                 235                 240
Leu Glu Val Ala Trp Thr Pro Gly Leu Ser Gly Ile Tyr Pro Leu Thr
                245                 250                 255
His Cys Thr Leu Gln Ala Val Leu Ser Asp Asp Gly Met Gly Ile Gln
            260                 265                 270
Ala Gly Glu Pro Asp Pro Pro Glu Glu Pro Leu Thr Ser Gln Ala Ser
            275                 280                 285
Val Pro Pro His Gln Leu Arg Leu Gly Ser Leu His Pro His Thr Pro
        290                 295                 300
Tyr His Ile Arg Val Ala Cys Thr Ser Ser Gln Gly Pro Ser Ser Trp
305                 310                 315                 320
Thr His Trp Leu Pro Val Glu Thr Pro Glu Gly Val Pro Leu Gly Pro
                325                 330                 335
Pro Glu Asn Ile Ser Ala Thr Arg Asn Gly Ser Gln Ala Phe Val His
            340                 345                 350
Trp Gln Glu Pro Arg Ala Pro Leu Gln Gly Thr Leu Leu Gly Tyr Arg
        355                 360                 365
Leu Ala Tyr Gln Gly Gln Asp Thr Pro Glu Val Leu Met Asp Ile Gly
    370                 375                 380
Leu Arg Gln Glu Val Thr Leu Glu Leu Gln Gly Asp Gly Ser Val Ser
385                 390                 395                 400
Asn Leu Thr Val Cys Val Ala Ala Tyr Thr Ala Ala Gly Asp Gly Pro
                405                 410                 415
Trp Ser Leu Pro Val Pro Leu Glu Ala Trp Arg Pro Gly Gln Ala Gln
```

-continued

```
                420             425             430
Pro Val His Gln Leu Val Lys Glu Pro Ser Thr Pro Ala Phe Ser Trp
            435                 440                 445
Pro Trp Trp Tyr Val Leu Leu Gly Ala Val Val Ala Ala Ala Cys Val
            450                 455                 460
Leu Ile Leu Ala Leu Phe Leu Val His Arg Arg Lys Lys Glu Thr Arg
465                 470                 475                 480
Tyr Gly Glu Val Phe Glu Pro Thr Val Glu Arg Gly Glu Leu Val Val
                485                 490                 495
Arg Tyr Arg Val Arg Lys Ser Tyr Ser Arg Arg Thr Thr Glu Ala Thr
            500                 505                 510
Leu Asn Ser Leu Gly Ile Ser Glu Glu Leu Lys Glu Lys Leu Arg Asp
            515                 520                 525
Val Met Val Asp Arg His Lys Val Ala Leu Gly Lys Thr Leu Gly Glu
            530                 535                 540
Gly Glu Phe Gly Ala Val Met Glu Gly Gln Leu Asn Gln Asp Asp Ser
545                 550                 555                 560
Ile Leu Lys Val Ala Val Lys Thr Met Lys Ile Ala Ile Cys Thr Arg
                565                 570                 575
Ser Glu Leu Glu Asp Phe Leu Ser Glu Ala Val Cys Met Lys Glu Phe
            580                 585                 590
Asp His Pro Asn Val Met Arg Leu Ile Gly Val Cys Phe Gln Gly Ser
            595                 600                 605
Glu Arg Glu Ser Phe Pro Ala Pro Val Val Ile Leu Pro Phe Met Lys
            610                 615                 620
His Gly Asp Leu His Ser Phe Leu Leu Tyr Ser Arg Leu Gly Asp Gln
625                 630                 635                 640
Pro Val Tyr Leu Pro Thr Gln Met Leu Val Lys Phe Met Ala Asp Ile
                645                 650                 655
Ala Ser Gly Met Glu Tyr Leu Ser Thr Lys Arg Phe Ile His Arg Asp
                660                 665                 670
Leu Ala Ala Arg Asn Cys Met Leu Asn Glu Asn Met Ser Val Cys Val
            675                 680                 685
Ala Asp Phe Gly Leu Ser Lys Lys Ile Tyr Asn Gly Asp Tyr Tyr Arg
            690                 695                 700
Gln Gly Arg Ile Ala Lys Met Pro Val Lys Trp Ile Ala Ile Glu Ser
705                 710                 715                 720
Leu Ala Asp Arg Val Tyr Thr Ser Lys Ser Asp Val Trp Ser Phe Gly
                725                 730                 735
Val Thr Met Trp Glu Ile Ala Thr Arg Gly Gln Thr Pro Tyr Pro Gly
            740                 745                 750
Val Glu Asn Ser Glu Ile Tyr Asp Tyr Leu Arg Gln Gly Asn Arg Leu
            755                 760                 765
Lys Gln Pro Ala Asp Cys Leu Asp Gly Leu Tyr Ala Leu Met Ser Arg
            770                 775                 780
Cys Trp Glu Leu Asn Pro Gln Asp Arg Pro Ser Phe Thr Glu Leu Arg
785                 790                 795                 800
Glu Asp Leu Glu Asn Thr Leu Lys Ala Leu Pro Pro Ala Gln Glu Pro
                805                 810                 815
Asp Glu Ile Leu Tyr Val Asn Met Asp Glu Gly Gly Gly Tyr Pro Glu
                820                 825                 830
Pro Pro Gly Ala Ala Gly Gly Ala Asp Pro Pro Thr Gln Pro Asp Pro
            835                 840                 845
```

Lys Asp Ser Cys Ser Cys Leu Thr Ala Ala Glu Val His Pro Ala Gly
              850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 3
<211> LENGTH: 1338
<212> TYPE: DNA
<213> ORGANISM: Artificial Sequence
<220> FEATURE:
<223> OTHER INFORMATION: V77-2a37.1 heavy chain cDNA

<400> SEQUENCE: 3

```
cagctgcagc tgcaggagtc gggcccagga ctggtgaggc cttcggagac cctgtccctc      60
acctgcactg tctctggtgt ctccatcacc aatagcagtt accactgggg ctggatccgc     120
cagcccccag ggaaggggct ggagtggatt gggagtatct tttataatgg gaacaccttc     180
ttcaacccgt ccctcaagag tcgagtcacc ttatccgtcg acacgtccaa gaaccaattc     240
tccctgaaac tgagtcctgt gaccgccgca gacacggctg tgtattactg tgagagacag     300
gataactgga acttccggca ctactttaac tattggggcc agggaaccct ggtcaccgtc     360
tcctcagcca aaacgacacc cccatctgtc tatccactgg cccctggatc tgctgcccaa     420
actaactcca tggtgaccct gggatgcctg gtcaagggct atttccctga gccagtgaca     480
gtgacctgga actctggatc cctgtccagc ggtgtgcaca ccttcccagc tgtcctgcag     540
tctgacctct acactctgag cagctcagtg actgtcccct ccagcacctg cccagcgag      600
accgtcacct gcaacgttgc ccacccggcc agcagcacca aggtggacaa gaaaattgtg     660
cccagggatt gtggttgtaa gccttgcata tgtacagtcc agaagtatc atctgtcttc      720
atcttccccc caaagcccaa ggatgtgctc accattactc tgactcctaa ggtcacgtgt     780
gttgtggtag acatcagcaa ggatgatccc gaggtccagt tcagctggtt tgtagatgat     840
gtggaggtgc acacagctca gacgcaaccc cgggaggagc agttcaacag cactttccgc     900
tcagtcagtg aacttcccat catgcaccag gactggctca atggcaagga gttcaaatgc     960
agggtcaaca gtgcagcttt ccctgccccc atcgagaaaa ccatctccaa aaccaaaggc    1020
agaccgaagg ctccacaggt gtacaccatt ccacctccca aggagcagat ggccaaggat    1080
aaagtcagtc tgacctgcat gataacagac ttcttccctg aagacattac tgtggagtgg    1140
cagtggaatg ggcagccagc ggagaactac aagaacactc agcccatcat ggacacagat    1200
ggctcttact cgtctacag caagctcaat gtgcagaaga caactgggag gcaggaaat     1260
actttcacct gctctgtgtt acatgagggt ctgcacaacc accatactga aagagcctc     1320
tcccactctc ctggtaaa                                                 1338
```

<210> SEQ ID NO 4
<211> LENGTH: 446
<212> TYPE: PRT
<213> ORGANISM: Artificial Sequence
<220> FEATURE:
<223> OTHER INFORMATION: V77-2a37.1 heavy chain amino acid

<400> SEQUENCE: 4

Gln Leu Gln Leu Gln Glu Ser Gly Pro Gly Leu Val Arg Pro Ser Glu
1               5                   10                  15

-continued

```
Thr Leu Ser Leu Thr Cys Thr Val Ser Gly Val Ser Ile Thr Asn Ser
             20                  25                  30

Ser Tyr His Trp Gly Trp Ile Arg Gln Pro Pro Gly Lys Gly Leu Glu
             35                  40                  45

Trp Ile Gly Ser Ile Phe Tyr Asn Gly Asn Thr Phe Phe Asn Pro Ser
             50                  55                  60

Leu Lys Ser Arg Val Thr Leu Ser Val Asp Thr Ser Lys Asn Gln Phe
 65                  70                  75                  80

Ser Leu Lys Leu Ser Pro Val Thr Ala Ala Asp Thr Ala Val Tyr Tyr
             85                  90                  95

Cys Glu Arg Gln Asp Asn Trp Asn Phe Arg His Tyr Phe Asn Tyr Trp
            100                 105                 110

Gly Gln Gly Thr Leu Val Thr Val Ser Ser Ala Lys Thr Thr Pro Pro
            115                 120                 125

Ser Val Tyr Pro Leu Ala Pro Gly Ser Ala Ala Gln Thr Asn Ser Met
            130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
            165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
            195                 200                 205

Pro Ala Ser Ser Thr Lys Val Asp Lys Lys Ile Val Pro Arg Asp Cys
            210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
            245                 250                 255

Lys Val Thr Cys Val Val Asp Ile Ser Lys Asp Asp Pro Glu Val
            260                 265                 270

Gln Phe Ser Trp Phe Val Asp Asp Val Glu Val His Thr Ala Gln Thr
            275                 280                 285

Gln Pro Arg Glu Glu Gln Phe Asn Ser Thr Phe Arg Ser Val Ser Glu
            290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
            325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
            355                 360                 365

Thr Asp Phe Phe Pro Glu Asp Ile Thr Val Glu Trp Gln Trp Asn Gly
            370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
            405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
```

<210> SEQ ID NO 5
<211> LENGTH: 639
<212> TYPE: DNA
<213> ORGANISM: Artificial Sequence
<220> FEATURE:
<223> OTHER INFORMATION: V77-2a37.1 light chain cDNA

<400> SEQUENCE: 5

```
gacatccaga tgacccagtc tccttccacc ctgtctgcat ctgtcggaga cagagtcacc      60
atcacttgcc gggccagtca gagtattagt aactggttgg cctggtatca gcagaaacca     120
gggaaagccc ctaaactcct gatctataag gcgtctagtt tagaaagtgg ggtcccatca     180
aggttcagcg gcagtggatc tgggacagag ttcactctca ccatcagcag cctgcagcct     240
gatgattttg ctacttatta ctgccaacag tataatagtt attacacttt tggccagggg     300
accaagctgg agatcaagcg ggctgatgct gcaccaactg tatccatctt cccaccatcc     360
agtgagcagt taacatctgg aggtgcctca gtcgtgtgct tcttgaacaa cttctacccc     420
aaagacatca atgtcaagtg gaagattgat ggcagtgaac gacaaaatgg cgtcctgaac     480
agttggactg atcaggacag caaagacagc acctacagca tgagcagcac cctcacgttg     540
accaaggacg agtatgaacg acataacagc tatacctgtg aggccactca caagacatca     600
acttcaccca ttgtcaagag cttcaacagg aatgagtgt                           639
```

<210> SEQ ID NO 6
<211> LENGTH: 213
<212> TYPE: PRT
<213> ORGANISM: Artificial Sequence
<220> FEATURE:
<223> OTHER INFORMATION: V77-2a37.1 light chain amino acid

<400> SEQUENCE: 6

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Tyr Thr
                85                  90                  95

Phe Gly Gln Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190
```

Cys Glu Ala Thr His Lys Thr Ser Thr Ser Pro Ile Val Lys Ser Phe
            195                 200                 205

Asn Arg Asn Glu Cys
    210

<210> SEQ ID NO 7
<211> LENGTH: 446
<212> TYPE: PRT
<213> ORGANISM: Artificial Sequence
<220> FEATURE:
<223> OTHER INFORMATION: V77-2a37.1 heavy chain amino acid

<400> SEQUENCE: 7

Gln Leu Gln Leu Gln Glu Ser Gly Pro Gly Leu Val Arg Pro Ser Glu
1               5                   10                  15

Thr Leu Ser Leu Thr Cys Thr Val Ser Gly Val Ser Ile Thr Asn Ser
            20                  25                  30

Ser Tyr His Trp Gly Trp Ile Arg Gln Pro Pro Gly Lys Gly Leu Glu
        35                  40                  45

Trp Ile Gly Ser Ile Phe Tyr Asn Gly Asn Thr Phe Phe Asn Pro Ser
50                  55                  60

Leu Lys Ser Arg Val Thr Leu Ser Val Asp Thr Ser Lys Asn Gln Phe
65                  70                  75                  80

Ser Leu Lys Leu Ser Pro Val Thr Ala Ala Asp Thr Ala Val Tyr Tyr
            85                  90                  95

Cys Glu Arg Gln Asp Asn Trp Asn Phe Arg His Tyr Phe Asn Tyr Trp
        100                 105                 110

Gly Gln Gly Thr Leu Val Thr Val Ser Ser Ala Lys Thr Thr Pro Pro
    115                 120                 125

Ser Val Tyr Pro Leu Ala Pro Gly Ser Ala Ala Gln Thr Asn Ser Met
130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
            165                 170                 175

Ala Val Leu Gln Ser Asp Leu Tyr Thr Leu Ser Ser Ser Val Thr Val
        180                 185                 190

Pro Ser Ser Thr Trp Pro Ser Glu Thr Val Thr Cys Asn Val Ala His
    195                 200                 205

Pro Ala Ser Ser Thr Lys Val Asp Lys Lys Ile Val Pro Arg Asp Cys
210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
            245                 250                 255

Lys Val Thr Cys Val Val Val Asp Ile Ser Lys Asp Asp Pro Glu Val
        260                 265                 270

Gln Phe Ser Trp Phe Val Asp Asp Val Glu Val His Thr Ala Gln Thr
    275                 280                 285

Gln Pro Arg Glu Glu Gln Phe Asn Ser Thr Phe Arg Ser Val Ser Glu
290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
            325                 330                 335

Lys Thr Lys Gly Arg Pro Lys Ala Pro Gln Val Tyr Thr Ile Pro Pro
                340                 345                 350

Pro Lys Glu Gln Met Ala Lys Asp Lys Val Ser Leu Thr Cys Met Ile
            355                 360                 365

Thr Asp Phe Phe Pro Glu Asp Ile Thr Val Glu Trp Gln Trp Asn Gly
        370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445

<210> SEQ ID NO 8
<211> LENGTH: 122
<212> TYPE: PRT
<213> ORGANISM: Artificial Sequence
<220> FEATURE:
<223> OTHER INFORMATION: V77-2a37.1 heavy chain variable region

<400> SEQUENCE: 8

Gln Leu Gln Leu Gln Glu Ser Gly Pro Gly Leu Val Arg Pro Ser Glu
1               5                   10                  15

Thr Leu Ser Leu Thr Cys Thr Val Ser Gly Val Ser Ile Thr Asn Ser
            20                  25                  30

Ser Tyr His Trp Gly Trp Ile Arg Gln Pro Pro Gly Lys Gly Leu Glu
        35                  40                  45

Trp Ile Gly Ser Ile Phe Tyr Asn Gly Asn Thr Phe Phe Asn Pro Ser
    50                  55                  60

Leu Lys Ser Arg Val Thr Leu Ser Val Asp Thr Ser Lys Asn Gln Phe
65                  70                  75                  80

Ser Leu Lys Leu Ser Pro Val Thr Ala Ala Asp Thr Ala Val Tyr Tyr
                85                  90                  95

Cys Glu Arg Gln Asp Asn Trp Asn Phe Arg His Tyr Phe Asn Tyr Trp
            100                 105                 110

Gly Gln Gly Thr Leu Val Thr Val Ser Ser
        115                 120

<210> SEQ ID NO 9
<211> LENGTH: 213
<212> TYPE: PRT
<213> ORGANISM: Artificial Sequence
<220> FEATURE:
<223> OTHER INFORMATION: V77-2a37.1 light chain

<400> SEQUENCE: 9

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro

```
                65                  70                  75                  80
Asp Asp Phe Ala Thr Tyr Tyr Cys Gln Gln Tyr Asn Ser Tyr Tyr Thr
                    85                  90                  95

Phe Gly Gln Gly Thr Lys Leu Glu Ile Lys Arg Ala Asp Ala Ala Pro
                100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
                195                 200                 205

Asn Arg Asn Glu Cys
            210

<210> SEQ ID NO 10
<211> LENGTH: 107
<212> TYPE: PRT
<213> ORGANISM: Artificial Sequence
<220> FEATURE:
<223> OTHER INFORMATION: V77-2a37.1 light chain variable region

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Tyr Thr
                85                  90                  95

Phe Gly Gln Gly Thr Lys Leu Glu Ile Lys Arg
                100                 105

<210> SEQ ID NO 11
<211> LENGTH: 11
<212> TYPE: PRT
<213> ORGANISM: Artificial Sequence
<220> FEATURE:
<223> OTHER INFORMATION: CDR-L1

<400> SEQUENCE: 11

Arg Ala Ser Gln Ser Ile Ser Asn Trp Leu Ala
1               5                   10

<210> SEQ ID NO 12
<211> LENGTH: 7
<212> TYPE: PRT
<213> ORGANISM: Artificial Sequence
<220> FEATURE:
```

```
<223> OTHER INFORMATION: CDR-L2

<400> SEQUENCE: 12

Lys Ala Ser Ser Leu Glu Ser
1               5

<210> SEQ ID NO 13
<211> LENGTH: 8
<212> TYPE: PRT
<213> ORGANISM: Artificial Sequence
<220> FEATURE:
<223> OTHER INFORMATION: CDR-L3

<400> SEQUENCE: 13

Gln Gln Tyr Asn Ser Tyr Tyr Thr
1               5

<210> SEQ ID NO 14
<211> LENGTH: 11
<212> TYPE: PRT
<213> ORGANISM: Artificial Sequence
<220> FEATURE:
<223> OTHER INFORMATION: CDR-L1

<400> SEQUENCE: 14

Arg Ala Ser Gln Ser Ile Ser Asn Trp Leu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: CDR-L2

<400> SEQUENCE: 15

Lys Ala Ser Ser Leu Glu Ser
1               5

<210> SEQ ID NO 16
<211> LENGTH: 8
<212> TYPE: PRT
<213> ORGANISM: Artificial Sequence
<220> FEATURE:
<223> OTHER INFORMATION: CDR-L3

<400> SEQUENCE: 16

Gln Gln Tyr Asn Ser Tyr Tyr Thr
1               5

<210> SEQ ID NO 17
<211> LENGTH: 7
<212> TYPE: PRT
<213> ORGANISM: Artificial Sequence
<220> FEATURE:
<223> OTHER INFORMATION: CDR-L1

<400> SEQUENCE: 17

Ser Asn Trp Leu Ala Trp Tyr
1               5

<210> SEQ ID NO 18
<211> LENGTH: 10
<212> TYPE: PRT
<213> ORGANISM: Artificial Sequence
<220> FEATURE:
<223> OTHER INFORMATION: CDR-L2
```

```
<400> SEQUENCE: 18

Leu Leu Ile Tyr Lys Ala Ser Ser Leu Glu
1               5                   10

<210> SEQ ID NO 19
<211> LENGTH: 7
<212> TYPE: PRT
<213> ORGANISM: Artificial Sequence
<220> FEATURE:
<223> OTHER INFORMATION: CDR-L3

<400> SEQUENCE: 19

Gln Gln Tyr Asn Ser Tyr Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: CDR-H1

<400> SEQUENCE: 20

Asn Ser Ser Tyr His Trp Gly
1               5

<210> SEQ ID NO 21
<211> LENGTH: 7
<212> TYPE: PRT
<213> ORGANISM: Artificial Sequence
<220> FEATURE:
<223> OTHER INFORMATION: CDR-H1

<400> SEQUENCE: 21

Asn Ser Ser Tyr His Trp Gly
1               5

<210> SEQ ID NO 22
<211> LENGTH: 16
<212> TYPE: PRT
<213> ORGANISM: Artificial Sequence
<220> FEATURE:
<223> OTHER INFORMATION: CDR-H2

<400> SEQUENCE: 22

Ser Ile Phe Tyr Asn Gly Asn Thr Phe Phe Asn Pro Ser Leu Lys Ser
1               5                   10                  15

<210> SEQ ID NO 23
<211> LENGTH: 12
<212> TYPE: PRT
<213> ORGANISM: Artificial Sequence
<220> FEATURE:
<223> OTHER INFORMATION: CDR-H3

<400> SEQUENCE: 23

Gln Asp Asn Trp Asn Phe Arg His Tyr Phe Asn Tyr
1               5                   10

<210> SEQ ID NO 24
<211> LENGTH: 9
<212> TYPE: PRT
<213> ORGANISM: Artificial Sequence
<220> FEATURE:
<223> OTHER INFORMATION: CDR-H1
```

```
<400> SEQUENCE: 24

Gly Val Ser Ile Thr Asn Ser Ser Tyr
1               5

<210> SEQ ID NO 25
<211> LENGTH: 9
<212> TYPE: PRT
<213> ORGANISM: Artificial Sequence
<220> FEATURE:
<223> OTHER INFORMATION: CDR-H1

<400> SEQUENCE: 25

Gly Val Ser Ile Thr Asn Ser Ser Tyr
1               5

<210> SEQ ID NO 26
<211> LENGTH: 5
<212> TYPE: PRT
<213> ORGANISM: Artificial Sequence
<220> FEATURE:
<223> OTHER INFORMATION: CDR-H2

<400> SEQUENCE: 26

Phe Tyr Asn Gly Asn
1               5

<210> SEQ ID NO 27
<211> LENGTH: 12
<212> TYPE: PRT
<213> ORGANISM: Artificial Sequence
<220> FEATURE:
<223> OTHER INFORMATION: CDR-H3

<400> SEQUENCE: 27

Gln Asp Asn Trp Asn Phe Arg His Tyr Phe Asn Tyr
1               5                   10

<210> SEQ ID NO 28
<211> LENGTH: 8
<212> TYPE: PRT
<213> ORGANISM: Artificial Sequence
<220> FEATURE:
<223> OTHER INFORMATION: CDR-H1

<400> SEQUENCE: 28

Thr Asn Ser Ser Tyr His Trp Gly
1               5

<210> SEQ ID NO 29
<211> LENGTH: 8
<212> TYPE: PRT
<213> ORGANISM: Artificial Sequence
<220> FEATURE:
<223> OTHER INFORMATION: CDR-H1

<400> SEQUENCE: 29

Thr Asn Ser Ser Tyr His Trp Gly
1               5

<210> SEQ ID NO 30
<211> LENGTH: 12
<212> TYPE: PRT
<213> ORGANISM: Artificial Sequence
<220> FEATURE:
<223> OTHER INFORMATION: CDR-H2

<400> SEQUENCE: 30
```

```
Trp Ile Gly Ser Ile Phe Tyr Asn Gly Asn Thr Phe
1               5                   10
```

<210> SEQ ID NO 31
<211> LENGTH: 13
<212> TYPE: PRT
<213> ORGANISM: Artificial Sequence
<220> FEATURE:
<223> OTHER INFORMATION: CDR-H3

<400> SEQUENCE: 31

```
Glu Arg Gln Asp Asn Trp Asn Phe Arg His Tyr Phe Asn
1               5                   10
```

US 10,787,516 B2

ANTIBODIES THAT BIND TO AXL PROTEINS

CROSS-REFERENCE TO RELATED APPLICATIONS

This application is a national stage application of PCT/US2016/033153, filed May 18, 2016, which claims priority to U.S. Provisional Patent Application No. 62/163,264, filed May 18, 2015, the contents of all of which are incorporated by reference in their entirety.

INCORPORATION BY REFERENCE OF SEQUENCE LISTING

The present application is being filed along with a Sequence Listing in electronic format. The Sequence Listing is provided as a file entitled 511582009840SEQLIST.TXT, created May 18, 2016 which is 32.4 kilobytes in size. The information in the electronic format of the Sequence Listing is incorporated by reference in its entirety.

STATEMENT OF RIGHTS TO INVENTIONS MADE UNDER FEDERALLY SPONSORED RESEARCH

Not applicable.

FIELD OF THE INVENTION

The invention described herein relates to antibodies and antigen-binding fragments thereof, that bind proteins, termed AXL. The invention further relates to prognostic, prophylactic, diagnostic and companion therapeutic methods and compositions useful in the treatment of cancers that express AXL.

BACKGROUND OF THE INVENTION

It is estimated that 1,660,290 men and women (854,790 men and 805,500 women) will be diagnosed with and 580,350 men and women will die of cancer of all sites in 2013. From 2006-2010, the median age at diagnosis for cancer of all sites was 66 years of age. The age-adjusted incidence rate was 463.0 per 100,000 men and women per year. These rates are based on cases diagnosed in 2006-2010 from 18 SEER geographic areas. From 2006-2010, the median age at death for cancer of all sites was 72 years of age. The age-adjusted death rate was 176.4 per 100,000 men and women per year. These rates are based on patients who died in 2006-2010 in the US. The overall 5-year relative survival for 2003-2009 from 18 SEER geographic areas was 65.8%.

Non-Hodgkin lymphomas (NHLs) can occur at any age and are often marked by lymph nodes that are larger than normal, fever, and weight loss. There are many different types of non-Hodgkin lymphoma. These types can be divided into aggressive (fast-growing) and indolent (slow-growing) types, and they can be formed from either B-cells or T-cells. B-cell non-Hodgkin lymphomas include Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. T-cell non-Hodgkin lymphomas include mycosis fungoides, anaplastic large cell lymphoma, and precursor T-lymphoblastic lymphoma. Lymphomas that occur after bone marrow or stem cell transplantation are usually B-cell non-Hodgkin lymphomas. Prognosis and treatment depend on the stage and type of disease.

It is estimated that 69,740 men and women (37,600 men and 32,140 women) will be diagnosed with and 19,020 men and women will die of non-Hodgkin lymphoma in 2013. From 2006-2010, the median age at diagnosis for non-Hodgkin lymphoma was 66 years of age. The age-adjusted incidence rate was 19.7 per 100,000 men and women per year. These rates are based on cases diagnosed in 2006-2010 from 18 SEER geographic areas. From 2006-2010, the median age at death for non-Hodgkin lymphoma was 76 years of age. The age-adjusted death rate was 6.4 per 100,000 men and women per year. These rates are based on patients who died in 2006-2010 in the US. The overall 5-year relative survival for 2003-2009 from 18 SEER geographic areas was 69.0%.

Leukemias are cancers that start in blood-forming tissue such as the bone marrow and causes large numbers of blood cells to be produced and enter the bloodstream. The major leukemias are comprised of Acute Lymphoblastic (ALL), Acute Myeloid (AML), Chronic Lymphocytic (CLL), Chronic Myelogenous (CML), and Hairy Cell (CLL) Leukemia.

For these leukemias as a group, it is estimated that 48,610 men and women (27,880 men and 20,730 women) will be diagnosed with and 23,720 men and women will die of leukemia in 2013. From 2006-2010, the median age at diagnosis for leukemia was 66 years of age. The age-adjusted incidence rate was 12.8 per 100,000 men and women per year. These rates are based on cases diagnosed in 2006-2010 from 18 SEER geographic areas. From 2006-2010, the median age at death for leukemia was 75 years of age. The age-adjusted death rate was 7.1 per 100,000 men and women per year. These rates are based on patients who died in 2006-2010 in the US. The overall 5-year relative survival for 2003-2009 from 18 SEER geographic areas was 56.0%.

CLL is the second most common type of leukemia in adults and it usually gets worse slowly. It often occurs during or after middle age and it rarely occurs in children. Patients with early-stage CLL are not treated with chemotherapy until they become symptomatic or display evidence of rapid progression of disease. Early initiation of chemotherapy has failed to show benefit in CLL and may even increase mortality. When chemotherapy is initiated, the nucleoside analogue fludarabine is the most commonly used first-line therapy in CLL. Combination regimens have shown improved response rates in several clinical trials and include the following: Fludarabine, cyclophosphamide, and rituximab (FCR); Pentostatin, cyclophosphamide, and rituximab (PCR); Fludarabine, cyclophosphamide, and mitoxantrone (FCM); Cyclophosphamide, vincristine, and prednisone (CVP); Cyclophosphamide, doxorubicin, vincristine, and prednisone (CHOP). It is estimated that 15,680 men and women (9,720 men and 5,960 women) will be diagnosed with and 4,580 men and women will die of chronic lymphocytic leukemia in 2013. From 2006-2010, the median age at diagnosis for chronic lymphocytic leukemia was 71 years of age. The age-adjusted incidence rate was 4.3 per 100,000 men and women per year. These rates are based on cases diagnosed in 2006-2010 from 18 SEER geographic areas. From 2006-2010, the median age at death for chronic lymphocytic leukemia was 79 years of age. The age-adjusted death rate was 1.4 per 100,000 men and women per year. These rates are based on patients who died in 2006-2010 in the US. The overall 5-year relative survival for 2003-2009 from 18 SEER geographic areas was 79.2%.

Acute myeloid leukemia (AML) is the most common type of acute leukemia among adults. Current treatment of AML should be sufficiently aggressive to achieve complete remission (CR) because partial remission offers no substantial survival benefit. Remission rates in adult AML are inversely related to age, with an expected remission rate of more than 65% for those younger than 60 years. Data suggest that once attained, duration of remission may be shorter in older patients. Patients that express the progenitor cell antigen CD34 and/or the P-glycoprotein (MOR1 gene product) have an inferior outcome. Cytogenetic analysis provides some of the strongest prognostic information available, predicting outcome of both remission induction and post remission therapy. Cytogenetic abnormalities that indicate a good prognosis include t(8; 21), inv(16) or t(16;16), and t(15;17). Normal cytogenetics portends average-risk AML. Patients with AML that is characterized by deletions of the long arms or monosomies of chromosomes 5 or 7; by translocations or inversions of chromosome 3, t(6; 9), t(9; 22); or by abnormalities of chromosome 11q23 have particularly poor prognoses with chemotherapy. It is estimated that 14,590 men and women (7,820 men and 6,770 women) will be diagnosed with and 10,370 men and women will die of acute myeloid leukemia in 2013. From 2006-2010, the median age at diagnosis for acute myeloid leukemia was 67 years of age. The age-adjusted incidence rate was 3.7 per 100,000 men and women per year. These rates are based on cases diagnosed in 2006-2010 from 18 SEER geographic areas. From 2006-2010, the median age at death for acute myeloid leukemia was 72 years of age. The age-adjusted death rate was 2.8 per 100,000 men and women per year. These rates are based on patients who died in 2006-2010 in the US. The overall 5-year relative survival for 2003-2009 from 18 SEER geographic areas was 24.2%. Note, all general cancer information was obtained from the NCI website and all statistics are based on SEER incidence and NCHS mortality statistics found within: Howlader N., et. al., SEER Cancer Statistics Review, 1975-2010, National Cancer Institute. Bethesda, Md., based on November 2012 SEER data submission, posted to the SEER web site, 2013.

The therapeutic utility of monoclonal antibodies (mAbs) (G. Kohler and C. Milstein, Nature 256:495-497 (1975)) is being realized. Monoclonal antibodies have now been approved as therapies in transplantation, cancer, infectious disease, cardiovascular disease and inflammation. Different isotypes have different effector functions. Such differences in function are reflected in distinct 3-dimensional structures for the various immunoglobulin isotypes (P. M. Alzari et al., Annual Rev. Immunol., 6:555-580 (1988)).

Furthermore, recent years, monoclonal antibodies are reported to be used for Companion diagnostics (Sai-Hong Ignatius Ou, et al, Front Oncol. 2014; 4: 58). Zhang firstly reports that activation of the AXL kinase causes resistance to EGFR-targeted therapy in lung cancer (Nature Genetics 44,852-860(2012)) and AF154AXL rabbit polyAb (R&D Systems) is used for detecting AXL in lung cancer patients (US 20140121126).

Because mice are convenient for immunization and recognize most human antigens as foreign, mAbs against human targets with therapeutic potential have typically been of murine origin. However, murine mAbs have inherent disadvantages as human therapeutics. They require more frequent dosing as mAbs have a shorter circulating half-life in humans than human antibodies. More critically, the repeated administration of murine antibodies to the human immune system causes the human immune system to respond by recognizing the mouse protein as a foreign and generating a human anti-mouse antibody (HAMA) response. Such a HAMA response may result in allergic reaction and the rapid clearing of the murine antibody from the system thereby rendering the treatment by murine antibody useless. To avoid such affects, attempts to create human immune systems within mice have been attempted.

Initial attempts hoped to create transgenic mice capable of responding to antigens with antibodies having human sequences (See Bruggemann et al., Proc. Nat'l. Acad. Sci. USA 86:6709-6713 (1989)), but were limited by the amount of DNA that could be stably maintained by available cloning vehicles. The use of yeast artificial chromosome (YAC) cloning vectors led the way to introducing large germline fragments of human Ig locus into transgenic mammals. Essentially a majority of the human V, D, and J region genes arranged with the same spacing found in the human genome and the human constant regions were introduced into mice using YACs. One such transgenic mouse strain is known as XenoMouse® mice and is commercially available from Amgen Fremont, Inc. (Fremont Calif.).

Additionally, antibodies can be prepared using VelocImmune® transgenic mice into which genomic sequences bearing endogenous mouse variable segments at the immunoglobulin heavy chain (VH, DH, and JH segments) and/or kappa light chain (VK and JK) loci have been replaced, in whole or in part, with human genomic sequences bearing unrearranged germline variable segments of the human immunoglobulin heavy chain (VH, DH, and JH) and/or kappa light chain (VK and JK) loci (Regeneron, Tarrytown, N.Y.). See, for example, U.S. Pat. Nos. 6,586,251, 6,596,541, 7,105,348, 6,528,313, 6,638,768, and 6,528,314.

SUMMARY OF THE INVENTION

The invention provides antibodies and antigen-binding fragments thereof that bind to AXL proteins and polypeptide fragments of AXL proteins. In some embodiments, the invention comprises fully human antibodies.

The invention further provides various immunogenic or therapeutic compositions, such as antibodies labelled with an imaging agent, and strategies for diagnosing, and treating cancers that express AXL such as cancers of tissues listed in Table I.

BRIEF DESCRIPTION OF THE FIGURES

FIG. 1. The cDNA (SEQ ID NO: 1) and amino acid sequence (SEQ ID NO: 2) of AXL is shown in FIG. 1. The start methionine is underlined. The open reading frame extends from nucleic acid 191-2875 including the stop codon.

FIG. 2A. Nucleic Acid and Amino Acid sequences of AXL antibodies. The cDNA (SEQ ID NO: 3) and amino acid sequence (SEQ ID NO: 4) of V77-2a37.1 heavy chain. Double-underlined is the heavy chain variable region, and underlined is the heavy chain mouse IgG1 constant region.

FIG. 2B. Nucleic Acid and Amino Acid sequences of AXL antibodies. The cDNA (SEQ ID NO: 5) and amino acid sequence (SEQ ID NO: 6) of V77-2a37.1 light chain. Double-underlined is the light chain variable region, and underlined is the mouse kappa constant region.

FIG. 3A. Amino Acid sequences of V77-2a37.1 antibodies. The amino acid sequence of the V77-2a37.1 heavy chain (SEQ ID NO: 7). The CDR regions (based on kabat numbering) are Italicized. Double-underlined is the heavy chain variable region (SEQ ID NO: 8), and underlined is the mouse IgG1 constant region.

FIG. 3B. Amino Acid sequences of V77-2a37.1 antibodies. The amino acid sequence of the V77-2a37.1 light chain (SEQ ID NO: 9). The CDR regions (based on kabat numbering) are Italicized. Double-underlined is the light chain variable region (SEQ ID NO: 10), and underlined is the mouse kappa constant region.

FIG. 4A. Alignment of V77-2a37.1 heavy chain variable region (SEQ ID NO: 8) to human Ig germline.

FIG. 4B. Alignment of V77-2a37.1 light chain variable region (SEQ ID NO: 10) to human Ig germline.

FIG. 5A and FIG. 5B show sarcoma cancer specimens. FIG. 5C and FIG. 5D show pancreatic cancer specimens. FIG. 5E and FIG. 5F show melanoma cancer specimens. FIG. 5G and FIG. 5H show ovarian cancer specimens. FIG. 5I and FIG. 5J show lung cancer specimens. AXL MAb denoted V77-2a37.1 is shown in FIGS. 5A, C, E, G, and I. A Negative control antibody is shown in FIGS. 5B, D, F, H, and J.

FIG. 6A(i), FIG. 6A(ii), and FIG. 6A(iii). Detection of AXL expression in FFPE cell block samples from three cell lines, FIG. 6A(i) NCI-H292 cells, FIG. 6A(ii) HCC827 cells, and FIG. 6A(iii) NCI-H727 cells, by RNA ISH.

FIG. 6B(i), FIG. 6B(ii), FIG. 6B(iii), FIG. 6B(iv), FIG. 6B(v), and FIG. 6B(vi). Detection of AXL expression in FFPE cell block samples from three cell lines (NCI-H292 cells, HCC827 cells, and NCI-H727 cells) by IHC using a Cell Signaling rabbit monoclonal antibody [C89E7] (FIGS. 6B(i), 6B(ii), and 6B(iii)) and a R&D goat polyclonal antibody [AF154] (FIGS. 6B(iv), 6B(v), and 6B(vi)). FIG. 6B(i): NCI-H292 cells with anti-AXL antibody [C89E7]. FIG. 6B(ii): HCC827 cells with anti-AXL antibody [C89E7]. FIG. 6B(iii): NCI-H727 cells with anti-AXL antibody [C89E7]. FIG. 6B(iv): NCI-H292 cells with anti-AXL antibody [AF154]. FIG. 6B(v): HCC827 cells with anti-AXL antibody [AF154]. FIG. 6B(vi): NCI-H727 with anti-AXL antibody [AF154].

DETAILED DESCRIPTION OF THE INVENTION

Outline of Sections

Figure 5A:
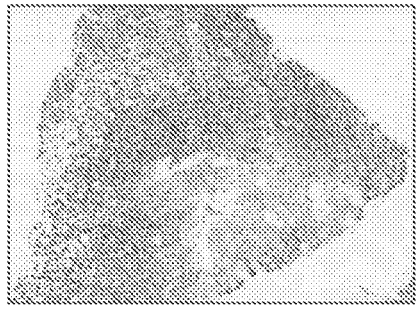
FIG. 5A-FIG. 5J. Detection of AXL protein in cancer patient specimens by IHC.

I.) Definitions
II.) AXL Antibodies
III.) Diagnosis of Cancer(s) Expressing AXL
IV.) Treatment of Cancer(s) Expressing AXL
V.) AXL as a Target for Antibody-based Therapy
VI.) AXL ADC Cocktails
VII.) Combination Therapy
VIII.) Kits/Articles of Manufacture I.) Definitions Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

When a trade name is used herein, reference to the trade name also refers to the product formulation, the generic drug, and the active pharmaceutical ingredient(s) of the trade name product, unless otherwise indicated by context.

The terms "advanced cancer", "locally advanced cancer", "advanced disease" and "locally advanced disease" mean cancers that have extended through the relevant tissue capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) cancer.

"Altering the native glycosylation pattern" is intended for purposes herein to mean deleting one or more carbohydrate moieties found in native sequence AXL (either by removing the underlying glycosylation site or by deleting the glycosylation by chemical and/or enzymatic means), and/or adding one or more glycosylation sites that are not present in the native sequence AXL. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a AXL-related protein). For example, an analog of a AXL protein can be specifically bound by an antibody or T cell that specifically binds to AXL.

The term "antibody" is used in the broadest sense unless clearly indicated otherwise. Therefore, an "antibody" can be naturally occurring or man-made such as monoclonal antibodies produced by conventional hybridoma technology. AXL antibodies comprise monoclonal and polyclonal antibodies as well as fragments containing the antigen-binding domain and/or one or more complementarity determining regions of these antibodies. As used herein, the term "antibody" refers to any form of antibody or fragment thereof that specifically binds AXL and/or exhibits the desired biological activity and specifically covers monoclonal antibodies (including full length monoclonal antibodies), polyclonal antibodies, multispecific antibodies (e.g., bispecific antibodies), and antibody fragments so long as they specifically bind AXL and/or exhibit the desired biological activity. Any specific antibody can be used in the methods and compositions provided herein. Thus, in one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody. For example, the antibody is a IgG1, IgG2, IgG3, or IgG4 antibody. The antibodies useful in the present methods and compositions can be generated in cell culture, in phage, or in various animals, including but not limited to cows, rabbits, goats, mice, rats, hamsters, guinea pigs, sheep, dogs, cats, monkeys, chimpanzees, and apes. Therefore, in one embodiment, an antibody of the present invention is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, ANTIBODY PRODUCTION: ESSENTIAL TECHNIQUES (Wiley, 1997); Shephard, et al., MONOCLONAL ANTIBODIES (Oxford University Press, 2000); Goding, MONOCLONAL ANTIBODIES: PRINCIPLES AND PRACTICE (Academic Press, 1993); and CURRENT PROTOCOLS IN IMMUNOLOGY (John Wiley & Sons, most recent edition). An antibody of the present invention can be modified by recombinant means to increase efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. No. 5,624,821, U.S. Pat. No. 6,194,551, Application No. WO 9958572; and Angal, et al., Mol. Immunol. 30: 105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to normal or defective AXL. See e.g., ANTIBODY ENGINEERING: A PRACTICAL APPROACH (Oxford University Press, 1996). Suitable antibodies with the desired biologic activities can be identified using the following in vitro assays including but not limited to: proliferation, migration, adhesion, soft agar growth, angiogenesis, cell-cell communication, apoptosis, transport, signal transduction, and the following in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays. They can also be used to quantify the AXL or its receptor.

The term "antigen-binding portion" or "antibody fragment" or "antigen binding fragment" of an antibody (or simply "antibody portion"), as used herein, refers to one or more fragments of a AXL antibody that retain the ability to specifically bind to an antigen (e.g., AXL and variants; FIG. 1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarily determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

As used herein, any form of the "antigen" can be used to generate an antibody that is specific for AXL. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may be genomic or non-genomic (e.g., cDNA) and encodes at least a portion of the extracellular domain. As used herein, the term "portion", in the context of an antigen, refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids. In one embodiment, the antibody of the methods and compositions herein specifically bind at least a portion of the extracellular domain of the AXL of interest.

The antibodies or antigen binding fragments thereof provided herein may be conjugated to a "bioactive agent." As used herein, the term "bioactive agent" refers to any synthetic or naturally occurring compound that binds the antigen and/or enhances or mediates a desired biological effect to enhance cell-killing toxins. In one embodiment, the binding fragments useful in the present invention are biologically active fragments. As used herein, the term "biologically active" refers to an antibody or antibody fragment that is capable of binding the desired antigenic epitope and directly or indirectly exerting a biologic effect. Direct effects include, but are not limited to the modulation, stimulation, and/or inhibition of a growth signal, the modulation, stimulation, and/or inhibition of an anti-apoptotic signal, the modulation, stimulation, and/or inhibition of an apoptotic or necrotic signal, modulation, stimulation, and/or inhibition the ADCC cascade, and modulation, stimulation, and/or inhibition the CDC cascade.

"Bispecific" antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al., Nature 305:537-39 (1983). Alternatively, bispecific antibodies can be prepared using chemical linkage. See, e.g., Brennan, et al., Science 229:81 (1985). Bispecific antibodies include bispecific antibody fragments. See, e.g., Hollinger, et al., Proc. Natl. Acad. Sci. U.S.A. 90:6444-48 (1993), Gruber, et al., J. Immunol. 152:5368 (1994).

The monoclonal antibodies described herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison et al., Proc. Natl. Acad. Sci. USA 81: 6851-6855 (1984)).

The term "Chemotherapeutic Agent" refers to all chemical compounds that are effective in inhibiting tumor growth. Non-limiting examples of chemotherapeutic agents include alkylating agents; for example, nitrogen mustards, ethyleneimine compounds and alkyl sulphonates; antimetabolites, for example, folic acid, purine or pyrimidine antagonists; mitotic inhibitors, for example, anti-tubulin agents such as vinca alkaloids, auristatins and derivatives of podophyllotoxin; cytotoxic antibiotics; compounds that damage or interfere with DNA expression or replication, for example, DNA minor groove binders; and growth factor receptor antagonists. In addition, chemotherapeutic agents include cytotoxic agents (as defined herein), antibodies, biological molecules and small molecules.

The term "compound" refers to and encompasses the chemical compound itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and/or solvates; however, this reference is for emphasis only, and is not to be construed as excluding other of the above forms as identified above.

The terms "complementarity determining region," and "CDR," are known in the art to refer to non-contiguous sequences of amino acids within antibody variable regions, which confer antigen specificity and binding affinity. In general, there are three (3) CDRs in each heavy chain variable region (CDR-H1, CDR-H2, CDR-H3) and three (3) CDRs in each light chain variable region (CDR-L1, CDR-L2, CDR-L3).

The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme), MacCallum et al., J. Mol. Biol. 262:732-745 (1996), "Antibody-antigen interactions: Contact analysis and binding site topography," *J. Mol. Biol.* 262, 732-745." (Contact" numbering scheme), Lefranc M P et al., "IMGT unique numbering for immunoglobulin and T cell receptor variable domains and Ig superfamily V-like domains," *Dev Comp Immunol*, 2003 January; 27 (1):55-77 ("IMGT" numbering scheme), and Honegger A and Plückthun A, "Yet another numbering scheme for immunoglobulin variable domains: an automatic modeling and analysis tool," *J Mol Biol,* 2001 Jun. 8; 309 (3):657-70, (AHo numbering scheme).

The boundaries of a given CDR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. Table V, infra, lists the positions of CDR-L1, CDR-L2, CDR-L3 and CDR-H1, CDR-H2, CDR-H3 as identified by the Kabat, Chothia, and Contact schemes, respectively. For CDR-H1, residue numbering is given listed using both the Kabat and Chothia numbering schemes.

Thus, unless otherwise specified, the terms "CDR" and "complementary determining region" of a given antibody or region thereof, such as a variable region, as well as individual CDRs (e.g., "CDR-H1, CDR-H2) of the antibody or region thereof, should be understood to encompass the complementary determining region as defined by any of the known schemes described herein above. In some instances, the scheme for identification of a particular CDR or CDRs is specified, such as the CDR as defined by the Kabat, Chothia, or Contact method. In other cases, the particular amino acid sequence of a CDR is given.

As used herein, the term "conservative substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., MOLECULAR BIOLOGY OF THE GENE, The Benjamin/Cummings Pub. Co., p. 224 (4th Edition 1987)). Such exemplary substitutions are preferably made in accordance with those set forth in Table II and Table(s) III(a-b). For example, such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III(a) herein; pages 13-15 "Biochemistry" 2nd ED. Lubert Stryer ed (Stanford University); Henikoff et al., PNAS 1992 Vol 89 10915-10919; Lei et al., J Biol Chem 1995 May 19; 270 (20):11882-6). Other substitutions are also permissible and may be determined empirically or in accord with known conservative substitutions.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Hollinger et al., Proc. Natl. Acad. Sci. USA 90:6444-48 (1993).

The term "deplete," in the context of the effect of a AXL binding agent on AXL-expressing cells, refers to a reduction in the number of or elimination of the AXL-expressing cells.

The term "gene product" is used herein to indicate a peptide/protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I", etc. In one embodiment, the cancer protein is encoded by a nucleic acid of FIG. 1. The cancer protein can be a fragment, or alternatively, be the full-length protein encoded by nucleic acids of FIG. 1. In one embodiment, a cancer amino acid sequence is used to determine sequence identity or similarity. In another embodiment, the sequences are naturally occurring allelic variants of a protein encoded by a nucleic acid of FIG. 1. In another embodiment, the sequences are sequence variants as further described herein.

"Heteroconjugate" antibodies are useful in the present methods and compositions. As used herein, the term "heteroconjugate antibody" refers to two covalently joined antibodies. Such antibodies can be prepared using known methods in synthetic protein chemistry, including using crosslinking agents. See, e.g., U.S. Pat. No. 4,676,980.

The term "homolog" refers to a molecule which exhibits homology to another molecule, by for example, having sequences of chemical residues that are the same or similar at corresponding positions.

In one embodiment, the antibody provided herein is a "human antibody." As used herein, the term "human antibody" refers to an antibody in which essentially the entire sequences of the light chain and heavy chain sequences, including the complementary determining regions (CDRs), are from human genes. In one embodiment, human monoclonal antibodies are prepared by the trioma technique, the human B-cell technique (see, e.g., Kozbor, et al., Immunol. Today 4: 72 (1983), EBV transformation technique (see, e.g., Cole et al. MONOCLONAL ANTIBODIES AND CANCER THERAPY 77-96 (1985)), or using phage display (see, e.g., Marks et al., J. Mol. Biol. 222:581 (1991)). In a specific embodiment, the human antibody is generated in a transgenic mouse. Techniques for making such partially to fully human antibodies are known in the art and any such techniques can be used. According to one particularly preferred embodiment, fully human antibody sequences are made in a transgenic mouse engineered to express human heavy and light chain antibody genes. An exemplary description of preparing transgenic mice that produce human antibodies found in Application No. WO 02/43478 and U.S. Pat. No. 6,657,103 (Abgenix) and its progeny. B cells from transgenic mice that produce the desired antibody can then be fused to make hybridoma cell lines for continuous production of the antibody. See, e.g., U.S. Pat. Nos. 5,569, 825; 5,625,126; 5,633,425; 5,661,016; and 5,545,806; and Jakobovits, Adv. Drug Del. Rev. 31:33-42 (1998); Green, et al., J. Exp. Med. 188:483-95 (1998).

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. See e.g., Cabilly U.S. Pat. No. 4,816,567; Queen et al. (1989) Proc. Nat'l Acad. Sci. USA 86:10029-10033; and ANTIBODY ENGINEERING: A PRACTICAL APPROACH (Oxford University Press 1996).

The terms "inhibit" or "inhibition of" as used herein means to reduce by a measurable amount, or to prevent entirely.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the AXL genes or that encode polypeptides other than AXL gene product or fragments thereof. A skilled artisan can readily employ nucleic acid isolation procedures to obtain an isolated AXL polynucleotide. A protein is said to be "isolated," for example, when physical, mechanical or chemical methods are employed to remove the AXL proteins from cellular constituents that are normally associated with the protein. A skilled artisan can readily employ standard purification methods to obtain an isolated AXL protein. Alternatively, an isolated protein can be prepared by chemical means.

Suitable "labels" include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. In addition, the antibodies provided herein can be useful as the antigen-binding component of fluorobodies. See e.g., Zeytun et al., Nat. Biotechnol. 21:1473-79 (2003).

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic cancer" and "metastatic disease" mean cancers that have spread to regional lymph nodes or to distant sites, and are meant to include stage D disease under the AUA system and stage T×N×M+ under the TNM system.

The term "modulator" or "test compound" or "drug candidate" or grammatical equivalents as used herein describe any molecule, e.g., protein, oligopeptide, small organic molecule, polysaccharide, polynucleotide, etc., to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways. In one embodiment, the modulator suppresses a cancer phenotype, e.g. to a normal tissue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates, or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or, has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, can be linked to each other or to other amino acids to create a longer peptide/protein. The modulatory peptides can be digests of naturally occurring proteins as is outlined above, random peptides, or "biased" random peptides. In a preferred embodiment, peptide/protein-based modulators are antibodies, and fragments thereof, as defined herein.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. In one embodiment, the polyclonal antibody contains a plurality of monoclonal antibodies with different epitope specificities, affinities, or avidities within a single antigen that contains multiple antigenic epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352: 624-628 (1991) and Marks et al., J. Mol. Biol. 222: 581-597 (1991), for example. These monoclonal antibodies will usually bind with at least a Kd of about 1 µM, more usually at least about 300 nM, typically at least about 30 nM, preferably at least about 10 nM, more preferably at least about 3 nM or better, usually determined by ELISA.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 1, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter (See, Table III) or single letter designations for amino acids are used. In the art, this term is often used interchangeably with "peptide" or "protein".

A "recombinant" DNA or RNA molecule is a DNA or RNA molecule that has been subjected to molecular manipulation in vitro.

As used herein, the term "single-chain Fv" or "scFv" or "single chain" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun, THE PHARMACOLOGY OF MONOCLONAL ANTIBODIES, vol. 113, Rosenburg and Moore eds. Springer-Verlag, New York, pp. 269-315 (1994).

As used herein, the terms "specific", "specifically binds" and "binds specifically" refer to the selective binding of the antibody to the target antigen epitope. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific. In one embodiment, a specific antibody is one that only binds the AXL antigen, but does not bind to the irrelevant antigen. In another embodiment, a specific antibody is one that binds human AXL antigen but does not bind a non-human AXL antigen with 70%, 75%, 80%, 85%, 90%, 91%, 92%, 93%, 94%, 95%, 96%, 97%, 98%, 99% or greater amino acid homology with the AXL antigen. In another embodiment, a specific antibody is one that binds human AXL antigen and binds murine AXL antigen, but with a higher degree of binding the human antigen. In another embodiment, a specific antibody is one that binds human AXL antigen and binds primate AXL antigen, but with a higher degree of binding the human antigen. In another embodiment, the specific antibody binds to human AXL antigen and any non-human AXL antigen, but with a higher degree of binding the human antigen or any combination thereof.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act.

The term "variant" refers to a molecule that exhibits a variation from a described type or norm, such as a protein that has one or more different amino acid residues in the corresponding position(s) of a specifically described protein (e.g. the AXL protein shown in FIG. 1.) An analog is an example of a variant protein. Splice isoforms and single nucleotides polymorphisms (SNPs) are further examples of variants.

The "AXL proteins" and/or "AXL related proteins" of the invention include those specifically identified herein (see, FIG. 1), as well as allelic variants, conservative substitution variants, analogs and homologs that can be isolated/generated and characterized without undue experimentation following the methods outlined herein or readily available in the art. Fusion proteins that combine parts of different AXL proteins or fragments thereof, as well as fusion proteins of a AXL protein and a heterologous polypeptide are also included. Such AXL proteins are collectively referred to as the AXL-related proteins, the proteins of the invention, or AXL. The term "AXL-related protein" refers to a polypeptide fragment or a AXL protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 280, 290, 300, 325, 325, 350, 375, 400, 425, 450, 475, 500, 525, 550, 575, 600, 625, 650, 675, 700, 725, 750, 775, 800, 810, 820, 830, 840, 841, 842, 843, 844, 845, 850, 855, 860, 865, 870, 875, 880, 885, 890, 891, 892, 893 or 894 or more amino acids.

II.) AXL Antibodies

Another aspect of the invention provides antibodies that bind to AXL-related proteins (See FIG. 1). In one embodiment, the antibody that binds to AXL-related proteins is an antibody that specifically binds to AXL protein comprising amino acid sequence of SEQ ID NO.: 2. The antibody that specifically binds to AXL protein comprising amino acid sequence of SEQ ID NO.: 2 includes antibodies that can bind to other AXL-related proteins. For example, antibodies that bind AXL protein comprising amino acid sequence of SEQ ID NO.: 2 can bind AXL-related proteins such as AXL variants and the homologs or analogs thereof.

AXL antibodies of the invention are particularly useful in cancer (see, e.g., Table I) prognostic assays, imaging, diagnostic, and therapeutic methodologies. Similarly, such antibodies are useful in the treatment, and/or prognosis of sarcoma, pancreatic, melanoma, ovarian, or lung and other cancers, to the extent AXL is also expressed or overexpressed in these other cancers. Moreover, intracellularly expressed antibodies (e.g., single chain antibodies) are therapeutically useful in treating cancers in which the expression of AXL is involved, such as advanced or metastatic sarcoma, pancreatic, melanoma, ovarian, or lung cancers or other advanced or metastatic cancers.

Various methods for the preparation of antibodies, specifically monoclonal antibodies, are well known in the art. For example, antibodies can be prepared by immunizing a suitable mammalian host using a AXL-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of AXL can also be used, such as a AXL GST-fusion protein. In a particular embodiment, a GST fusion protein comprising all or most of the amino acid sequence of FIG. 1 is produced, and then used as an immunogen to generate appropriate antibodies. In another embodiment, a AXL-related protein is synthesized and used as an immunogen.

In addition, naked DNA immunization techniques known in the art are used (with or without purified AXL-related protein or AXL expressing cells) to generate an immune response to the encoded immunogen (for review, see Donnelly et al., 1997, Ann. Rev. Immunol. 15: 617-648).

The amino acid sequence of a AXL protein as shown in FIG. 1 can be analyzed to select specific regions of the AXL protein for generating antibodies. For example, hydrophobicity and hydrophilicity analyses of a AXL amino acid sequence are used to identify hydrophilic regions in the AXL structure. Regions of a AXL protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Preferred methods for the generation of AXL antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a AXL immunogen is often conducted by injection over a suitable time period and with use of a suitable adjuvant, as is understood in the art. During the immunization schedule, titers of antibodies can be taken to determine adequacy of antibody formation.

AXL monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a AXL-related protein. When the appropriate immortalized cell culture is identified, the cells can be expanded and antibodies produced either from in vitro cultures or from ascites fluid.

The antibodies or fragments of the invention can also be produced by recombinant means. Regions that bind specifically to the desired regions of a AXL protein can also be produced in the context of chimeric or complementarity-determining region (CDR) grafted antibodies of multiple species origin. Humanized or human AXL antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

In a preferred embodiment, human monoclonal antibodies of the invention can be prepared using VelocImmune® mice into which genomic sequences beating endogenous mouse variable segments at the immunoglobulin heavy chain (VH, DH, and JH segments) and/or kappa light chain (VK and JK) loci have been replaced, in whole or in part, with human genomic sequences bearing unrearranged germline variable segments of the human immunoglobulin heavy chain (VH, DH, and JH) and/or kappa light chain (VK and JK) loci (Regeneron, Tarrytown, N.Y.). See, for example, U.S. Pat. Nos. 6,586,251, 6,596,541, 7,105,348, 6,528,313, 6,638,768, and 6,528,314.

In addition, human antibodies of the invention can be generated using the HuMAb mouse (Medarex, Inc.) which contains human immunoglobulin gene miniloci that encode unrearranged human heavy (mu and gamma) and kappa light chain immunoglobulin sequences, together with targeted mutations that inactivate the endogenous mu and kappa chain loci (see e.g., Lonberg, et al. (1994) Nature 368(6474): 856-859).

In another embodiment, fully human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", such mice are described in Tomizuka et al. (2000) Proc. Natl. Acad. Sci. USA 97:722-727 and PCT Publication WO 02/43478 to Tomizuka, et al.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Additionally, human antibodies of the present invention can be made with techniques using transgenic mice, inactivated for antibody production, engineered with human heavy and light chains loci referred to as Xenomouse® (Amgen Fremont, Inc.). An exemplary description of preparing transgenic mice that produce human antibodies can be found in U.S. Pat. No. 6,657,103. See, also, U.S. Pat. Nos. 5,569,825; 5,625,126; 5,633,425; 5,661,016; and 5,545,806; and Mendez, et. al. Nature Genetics, 15: 146-156 (1998); Kellerman, S. A. & Green, L. L., Curr. Opin. Biotechnol 13, 593-597 (2002).

In one embodiment, an AXL MAbs of the invention comprises heavy and light chain CDRs of an antibody designated V77-2a37.1, whereby the heavy chain variable region is set forth in FIG. 3A as SEQ ID NO: 8 and whereby the light chain variable region is set forth in FIG. 3B as SEQ ID NO: 10. In one aspect of invention, an AXL MAbs of the invention comprises a heavy chain comprising CDR-H1 consisting of residues 31-37 (SEQ ID NO: 20), CDR-H2 consisting of residues 50-65 (SEQ ID NO: 22) and CDR-H3 consisting of residues 95-102 (SEQ ID NO: 23) and a light chain comprising CDR-L1 consisting of residues 24-34 (SEQ ID NO: 11), a CDR-L2 consisting of residues 50-56 (SEQ ID NO: 12) and CDR-L3 consisting of residues 89-97 (SEQ ID NO: 13). In a preferred embodiment, an AXL MAbs of the invention comprises heavy and light chain variable regions of an antibody designated V77-2a37.1, whereby the heavy chain variable region is set forth in FIG. 3A as SEQ ID NO: 8 and whereby the light chain variable region is set forth in FIG. 3B as SEQ ID NO: 10. The MAbs of the inventions comprise heavy and light variable regions comprising amino acid sequences that are homologous to the amino acid sequences of the heavy and light chain variable regions of V77-2a37.1, and wherein the antibodies retain the desired functional properties of the AXL MAbs of the invention. It should be noted, as the constant region of the antibody of the invention, any subclass of constant region can be chosen. In one embodiment, human IgG2 constant region as the heavy chain constant region and human Ig kappa constant region as the light chain constant region can be used. In other embodiment, mouse IgG1 constant region as the heavy chain constant region and mouse Ig kappa constant region as the light chain constant region can be used.

Engineered antibodies of the invention include those in which modifications have been made to framework residues within $V_H$ and/or $V_L$ (e.g. to improve the properties of the antibody). Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis (e.g., "backmutated" from leucine to methionine). Such "backmutated" antibodies are also intended to be encompassed by the invention.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, a AXL MAb of the invention may be chemically modified (e.g., one or more chemical moieties can be attached to the antibody) or be modified to alter its glycosylation, again to alter one or more functional properties of the MAb. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the AXL MAb.

In another embodiment, the Fc hinge region of an antibody is mutated to decrease the biological half life of the AXL MAb. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the AXL MAb is modified to increase its biological half life. Various approaches are possible. For example, mutations can be introduced as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the AXL MAb. For example, one or more amino acids selected from amino acid specific residues can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

Reactivity of AXL antibodies with a AXL-related protein can be established by a number of well known means, including Western blot, immunoprecipitation, ELISA, and FACS analyses using, as appropriate, AXL-related proteins, AXL-expressing cells or extracts thereof. A AXL antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more AXL epitopes are generated using methods generally known in the art. Homodimeric antibodies can also be generated by cross-linking techniques known in the art (e.g., Wolff et al., Cancer Res. 53: 2560-2565).

In yet another preferred embodiment, the AXL MAb of the invention is an antibody comprising heavy and light chain of an antibody designated V77-2a37.1. In a preferred embodiment, V77-2a37.1 is conjugated to an imaging agent. In a further preferred embodiment, V77-2a37.1 is used in conjunction with a small molecule compound as a companion diagnostic (CDx).

III.) Diagnosis of Cancer(s) Expressing AXL

The AXL MAb of the invention can be used in the detection method of the presence of cancer in a subject, or in a diagnosis method of cancer in a subject. The example of cancer in the detection method or diagnosis method includes sarcoma, pancreatic cancer, melanoma, ovarian cancer, and lung cancer. In addition, the AXL MAb of the invention can be used in the detection method of AXL expression in sample obtained from a subject such as cancer patients. It is known that AXL expression in cancer cells relates to resistance to EGFR inhibitor (e.g, Erlotinib) in cancer patient which has undergone treatment by EGFR inhibitor. Therefore, the combination of AXL kinase inhibitor and EGFR inhibitor can be used for diminishment of EGFR inhibitor resistance and suppression of cancer growth. The AXL MAb of the invention can be used in a method for identifying a cancer patient who is positive for AXL expression, and therefore is subject to treatment by AXL kinase inhibitor and/or EGFR inhibitor. In one embodiment, the cancer is selected from the group consisting of sarcoma, pancreatic cancer, melanoma, ovarian cancer, and lung cancer. In one embodiment, the patient has undergone treatment by EGFR inhibitor and the cancer is resistant to EGFR inhibitor resistance.

The detection method comprises a step of detecting the existence of AXL protein in a sample obtained from a subject. As the sample obtained from a subject, substances collected from a subject (samples separated from a biological body), specifically, any type of collected tissues, body fluids (preferably blood), bronchoalveolar lavages, samples having undergone biopsy, cancer cells in urine, and sputum samples are used. In one preferable embodiment, biopsy samples collected from the affected site of organ (e.g., lung) of a subject can be used. It is also possible to use a specimen (FFPE) obtained by fixing the sample by using formalin and stabilizing the sample by embedding it in paraffin. Moreover, an FFPE slice obtained by cutting the FFPE into a thin slice may be used. If the FFPE slice is used, it is possible to directly detect AXL protein existing in the slice.

The step of detecting AXL protein can be conducted by using one of the methods known in the skilled in the art. For example, the detection may be performed by a method as a combination of immunoassay and enzymatic activity assay in which a solubilization solution derived from a sample obtained from a test subject (for example, a cancer tissue or a cancer cell obtained from a test subject) is prepared, and AXL protein contained in the solution is combined with AXL antibody of the invention. Furthermore, the detection may be performed by an immunohistostaining technique in which AXL protein contained in a sample (for example, an FFPE fragment) obtained from a test subject which has undergone pretreatment (for example, removal of paraffin) as appropriate is combined with the AXL antibody of the invention. Examples of these techniques include techniques such as enzymatic immunoassay, double antibody sandwich ELISA, fluorescence immunoassay, radioimmunoassay, Western blotting, and immunohistostaining.

In addition to the above embodiments, the below paragraphs describe additional antibodies, antigen binding fragments, and uses and methods using the same:

Described herein, e.g. in this first paragraph, are antibodies and antigen binding fragments of such antibodies that bind AXL protein, suitably human AXL protein. In certain embodiments, the antibodies and antigen binding fragments specifically bind AXL protein, suitably human AXL protein. Such antibodies comprise the complementary determining regions consisting of the amino acid sequences as set forth in the SEQ ID NOs shown in Table VI, as identified by the Kabat, Chothia, and Contact schemes. Thus, in one embodiment is an antibody or antigen binding fragment comprising a CDR-L1 consisting of the amino acid sequence set forth in SEQ ID NO:11, a CDR-L2 consisting of the amino acid sequence set forth in SEQ ID NO:12, a CDR-L3 consisting of the amino acid sequence set forth in SEQ ID NO:13, a CDR-H1 consisting of the amino acid sequence set forth in SEQ ID NO:20, a CDR-H2 consisting of the amino acid sequence set forth in SEQ ID NO:22, and a CDR-H3 consisting of the amino acid sequence set forth in SEQ ID NO:23. In an alternative embodiment is an antibody or antigen binding fragment comprising a CDR-L1 consisting of the amino acid sequence set forth in SEQ ID NO:14, a CDR-L2 consisting of the amino acid sequence set forth in SEQ ID NO:15, a CDR-L3 consisting of the amino acid sequence set forth in SEQ ID NO:16, a CDR-H1 consisting of the amino acid sequence set forth in SEQ ID NO:25, a CDR-H2 consisting of the amino acid sequence set forth in SEQ ID NO:26, and a CDR-H3 consisting of the amino acid sequence set forth in SEQ ID NO:27. In yet another alternative embodiment is an antibody or antigen binding fragment comprising a CDR-L1 consisting of the amino acid sequence set forth in SEQ ID NO:17, a CDR-L2 consisting of the amino acid sequence set forth in SEQ ID NO:18, a CDR-L3 consisting of the amino acid sequence set forth in SEQ ID NO:19, a CDR-H1 consisting of the amino acid sequence set forth in SEQ ID NO: 28, a CDR-H2 consisting of the amino acid sequence set forth in SEQ ID NO: 30, and a CDR-H3 consisting of the amino acid sequence set forth in SEQ ID NO: 31.

Another embodiment is an antibody or antigen binding fragment according to the preceding paragraph, wherein the antibody or antigen binding fragment comprises a heavy chain variable region consisting of the amino acid sequence set forth in SEQ ID NO: 8 and a light chain variable region consisting of the amino acid set forth in SEQ ID NO: 10.

Another embodiment, disclosed herein, e.g., in this third paragraph, are full length antibodies. Thus, one embodiment is an antibody or antigen binding fragment according to any one of the preceding paragraphs, wherein the antibody comprises a heavy chain consisting of the amino acid sequence set forth in SEQ ID NO: 7 and a light chain consisting of the amino acid sequence set forth in SEQ ID NO: 9.

Also disclosed herein, e.g. in this fourth paragraph, are antibodies that bind AXL protein, suitably human AXL protein, that have substantial sequence identity to those described in the preceding paragraphs. Thus, one embodiment of this paragraph is an antibody or antigen binding fragment thereof that has 90%, 91%, 92%, 93%, 94%, 95%, 96%, 97%, 98%, or 99% to an antibody or antigen binding fragment of any of the preceding paragraphs. In a further embodiment, the antibody or antigen binding fragment thereof has 95% or greater sequence identity to the antibody or antigen binding fragment according to any of the preceding paragraphs. In further embodiments, the antibodies or antigen binding fragments in the instant paragraph have amino acid changes that do not substantially change the binding affinity relative to the original unmodified sequence. In certain embodiments such antibodies or antigen binding fragments have about the same binding affinity, that is the antibody or antigen binding fragment of this instant paragraph specifically binds AXL protein with less than 1%, 2%, 3%, 4%, 5%, 6%, 7%, 8%, 10%, 11%, 12%, 13%, or 14%, or 15% change as compared to the binding affinity of the original antibody or antigen binding fragment according to any one of the preceding paragraphs. A further and suitable embodiment is an antibody or antigen binding fragment that has 99% sequence identity to the original antibody or fragment according to any one of the preceding paragraphs, and wherein any amino acid changes are not to a residue in any CDR regions, wherein the CDR regions are determined using Kabat numbering. In an alternative embodiment the antibody or antigen binding fragment has 99% sequence identity to the original antibody or fragment in the preceding paragraphs, and wherein any amino acid changes are not to a residue in any CDR regions, wherein the CDR regions are determined by Chothia numbering. In an alternative embodiment the antibody or antigen binding fragment has 99% sequence identity to the original antibody or fragment in the preceding paragraphs, and wherein any amino acid changes are not to a residue in any CDR regions, wherein the CDR regions are determined by the Contact method. In further embodiments, the antibody or antigen binding fragment with 99% sequence identity to the original antibody or antigen binding fragment of the preceding paragraph has about the same binding affinity as the original antibody or antigen binding fragment.

Another embodiment, as disclosed herein, e.g. in this fifth paragraph is the antibody or antigen binding fragment thereof according to any of the preceding paragraphs, wherein the fragment is an Fab, F(ab')2, Fv or scFv fragment. In certain embodiments an antigen binding fragment of this paragraph or any of the preceding paragraphs can be fused to a heterologous Fc region or a heterologous constant region resulting in a chimeric antibody.

Another embodiment, as disclosed herein, e.g. in this sixth paragraph, is the antibody or antigen binding fragment according to any of the preceding paragraphs, wherein the antibody or antigen binding fragment is a fully human antibody.

Another embodiment, as disclosed herein, e.g. in this seventh paragraph, is the antibody or antigen binding fragment according to any of the preceding paragraphs, wherein the antibody is an antibody designated V77-2a37.1.

Another embodiment, as disclosed herein, e.g. in this eighth paragraph, is one or more polynucleotides encoding the antibody or antigen binding fragment according to any one of the preceding paragraphs. In one embodiment, the heavy chain variable region or the heavy chain is encoded by one polynucleotide, and the light chain variable region or the light chain is encoded on a second polynucleotide. In a further embodiment, the one or more polynucleotides is a vector.

In further embodiments disclosed herein, e.g. in this ninth paragraph, are host cells comprising the one or more polynucleotides of the preceding paragraph. In one embodiment is a host cell comprising one vector comprising the heavy chain variable region or the heavy chain of an antibody or antigen binding fragment according to any one of paragraphs one to seven, and another vector comprising the light chain variable region or the light chain of an antibody or antigen binding fragment according to any one of paragraphs one to seven.

In a further embodiment as disclosed herein, e.g. in this tenth paragraph, is an antibody or antigen binding fragment thereof produced by the host cell of the preceding paragraph. In a further embodiment, the antibody or antigen binding fragment so produced is further isolated by one or more techniques known in the art, including ion exchange chromatography, HPLC, size exclusion chromatography, SDS PAGE, affinity chromatography, and the like. In a further embodiment, the antibody or antigen binding fragment is about 90% or more pure. Another embodiment as disclosed herein, e.g. in this tenth paragraph, is an antibody or antigen binding fragment thereof that competes for binding with the antibody or antigen binding fragment according to any one of paragraphs one to seven. In a further embodiment, the antibody that competes for binding in an ELISA assay comprising a multi-well plate coated with AXL protein, suitably human protein.

Another embodiment is the antibody or antigen binding fragment according to any one of paragraphs one to seven, or paragraph 10, wherein the antibody or antigen binding fragment is recombinantly produced.

Another embodiment is the antibody or antigen binding fragment according to any one of paragraphs one to seven, or paragraph 10, wherein the antibody or antigen binding fragment is conjugated to an imaging agent. In an alternative embodiment, the antibody or antigen binding fragment according to any of the preceding paragraphs is for use as an imaging agent. In a further embodiment in an antibody or antigen binding fragment of any one of the preceding paragraphs for use as in vivo imaging agent. In an alternative embodiment, antibody or antigen binding fragment of any one of the preceding paragraphs for use an ex vivo imaging agent, suitably for use in a detection assay; such assays include, but are not limited to, immunohistochemistry, immunocytochemistry, immunoassays, ELISAs (including double antibody sandwich ELISAs), and Western blotting. A further embodiment is an antibody or antigen binding fragment according to any of the preceding paragraphs, wherein the antibody or antigen binding fragment is conjugated, directly or indirectly, to one or more detection reagents. The assays may be qualitative or quantitative and employ any number of detection reagents, including but not limited to, radioactivity, fluorescence, chemiluminescence and may also involve enzyme linked detection using any of the preceding reagents.

In a different embodiment is the antibody or antigen binding fragment according to any one of paragraphs one to seven, or paragraph 10, for use as a companion diagnostic (CDx) to screen one or more patients for the diagnosis and/or treatment and/or management of cancer, suitably sarcoma, pancreatic cancer, melanoma, ovarian cancer, and lung cancer.

In a different embodiment is a method of detecting AXL expression in one or more tumor cells in a subject, comprising a step of contacting the antibody or antigen binding fragment according to any one of paragraphs one to seven, or paragraph 10, with a sample of one or more cells obtained from the subject. In a further embodiment, the subject is a human. In a further embodiment, the human in need of diagnosis and/or treatment of cancer. In a further embodiment, the one or more tumor cells are suitably cells of a solid organ tumor, suitably pancreatic, ovarian, lung, and skin. In an alternative embodiment, the one or more tumor cells are soft tissue cells of mesenchymal origin. In another embodiment, the one or more cells are selected from the group consisting of sarcoma cells, pancreatic tumor cells, melanoma cells, ovarian tumor cells, and lung tumor cells. In a further embodiment, the subject, suitably a human, was previously treated with an EGFR inhibitor. In a further embodiment, the subject, suitably a human, previously treated with an EGFR inhibitor was determined to have a cancer that did not substantially respond to an EGFR inhibitor, that is, an EGFR resistant cancer.

In a different embodiment is a method for identifying a subject, suitably a human, having one or more cancer cells which are positive for AXL expression, comprising contacting the antibody or antigen binding fragment according to any one of paragraphs one to seven, or paragraph 10, with a sample of one or more cells obtained from the subject, suitably a human, and detecting binding of the antibody or antigen binding fragment to AXL. In a further embodiment, the subject, suitably a human, was previously treated with an EGFR inhibitor. In a further embodiment, the subject, suitably a human, previously treated with an EGFR inhibitor was determined to have an EGFR resistant cancer.

In yet a different embodiment is a method of diagnosing cancer in a subject, suitably a human, the method comprising contacting the antibody or antigen binding fragment according to any one of paragraphs one to seven, or paragraph 10, with a sample of one or more cells obtained from the subject, suitably a human, detecting binding of the antibody or antigen binding fragment to AXL, and determining an increased level of AXL as compared to a control sample of one or more cells that are from normal, that is non-tumor or noncancerous, cells, and thereby diagnosing cancer. In a further embodiment, the subject, suitably a human, was previously treated with an EGFR inhibitor. In a further embodiment, the subject, suitably a human, previously treated with an EGFR inhibitor was determined to have an EGFR resistant cancer.

IV.) Treatment of Cancer(s) Expressing AXL

The identification of AXL as a protein that is normally expressed in a restricted set of tissues, but which is also expressed in cancers such as those listed in Table I, opens a number of therapeutic and diagnostic approaches to the treatment of such cancers.

Of note, targeted antitumor therapies have been useful even when the targeted protein is expressed on normal tissues, even vital normal organ tissues. A vital organ is one that is necessary to sustain life, such as the heart or colon. A non-vital organ is one that can be removed whereupon the individual is still able to survive. Examples of non-vital organs are ovary, breast, and prostate.

Expression of a target protein in normal tissue, even vital normal tissue, does not defeat the utility of a targeting agent for the protein as a therapeutic for certain tumors in which the protein is also overexpressed. For example, expression in vital organs is not in and of itself detrimental. In addition, organs regarded as dispensible, such as the prostate and ovary, can be removed without affecting mortality. Finally, some vital organs are not affected by normal organ expression because of an immunoprivilege. Immunoprivileged organs are organs that are protected from blood by a blood-organ barrier and thus are not accessible to immunotherapy. Examples of immunoprivileged organs are the brain and testis.

Accordingly, therapeutic approaches that inhibit the activity of a AXL protein are useful for patients suffering from a cancer that expresses AXL. These therapeutic approaches generally fall into three classes. The first class modulates AXL function as it relates to tumor cell growth leading to inhibition or retardation of tumor cell growth or inducing its killing. The second class comprises various methods for inhibiting the binding or association of a AXL protein with its binding partner or with other proteins. The third class comprises a variety of methods for inhibiting the transcription of a AXL gene or translation of AXL mRNA.

Accordingly, Cancer patients can be evaluated for the presence and level of AXL expression, preferably using immunohistochemical assessments of tumor tissue, quantitative AXL imaging, or other techniques that reliably indicate the presence and degree of AXL expression. Immunohistochemical analysis of tumor biopsies or surgical specimens is preferred for this purpose. Methods for immunohistochemical analysis of tumor tissues are well known in the art.

V.) AXL as a Target for Antibody-based Therapy

AXL is an attractive target for antibody-based therapeutic strategies. A number of antibody strategies are known in the art for targeting both extracellular and intracellular molecules (see, e.g., complement and ADCC mediated killing as well as the use of intrabodies). Because AXL is expressed by cancer cells of various lineages relative to corresponding normal cells, systemic administration of AXL-immunoreactive compositions are prepared that exhibit excellent sensitivity without toxic, non-specific and/or non-target effects caused by binding of the immunoreactive composition to non-target organs and tissues. Antibodies specifically reactive with domains of AXL are useful to treat AXL-expressing cancers systemically, preferably as antibody drug conjugates (i.e. ADCs) wherein the conjugate is with an imagin agent, toxin or therapeutic agent.

Those skilled in the art understand that antibodies can be used to specifically target and bind immunogenic molecules such as an immunogenic region of a AXL sequence shown in FIG. 1. In addition, skilled artisans understand that it is routine to conjugate antibodies to cytotoxic agents (see, e.g., Slevers et al. Blood 93:11 3678-3684 (Jun. 1, 1999)). When cytotoxic and/or therapeutic agents are delivered directly to cells, such as by conjugating them to antibodies specific for a molecule expressed by that cell (e.g. AXL), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an mammal having a tumor a biologically effective amount of a conjugate comprising a selected cytotoxic and/or therapeutic agent linked to a targeting agent (e.g. a AXL MAb, preferably V77-2a37.1) that binds to an antigen (e.g. AXL) expressed, accessible to binding or localized on the cell surfaces. A typical embodiment is a method of delivering a cytotoxic and/or therapeutic agent to a cell expressing AXL, comprising conjugating the cytotoxic agent to an antibody that immunospecifically binds to a AXL epitope, and, exposing the cell to the antibody drug conjugate (ADC). Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using AXL antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals) respectively, while others involve co-administration of antibodies and other therapeutic agents, such as Herceptin™ (trastuzu MAb) with paclitaxel (Genentech, Inc.). In a preferred embodiment, the antibodies will be conjugated an imaging agent. In a further preferred embodiment, the MAbs will be used as a companion diagnostic in conjunction with another compound for the treatment of disease.

Although AXL antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents.

AXL monoclonal antibodies that treat the cancers set forth in Table I include those that initiate a potent immune response against the tumor or those that are directly cytotoxic. In this regard, AXL monoclonal antibodies (MAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, AXL MAbs that exert a direct biological effect on tumor growth are useful to treat cancers that express AXL. Mechanisms by which directly cytotoxic MAbs act include: inhibition of cell growth, modulation of cellular differentiation, modulation of tumor angiogenesis factor profiles, and the induction of apoptosis. The mechanism(s) by which a particular AXL MAb exerts an anti-tumor effect is evaluated using any number of in vitro assays that evaluate cell death such as ADCC, complement-mediated cell lysis, and so forth, as is generally known in the art.

Accordingly, preferred monoclonal antibodies used in the therapeutic methods of the invention are those that are either fully human and that bind specifically to the target AXL antigen with high affinity.

VI.) AXL ADC Cocktails

Therapeutic methods of the invention contemplate the administration of single AXL ADCs as well as combinations, or cocktails, of different MAbs (i.e. AXL MAbs or Mabs that bind another protein). Such MAb cocktails can have certain advantages inasmuch as they contain MAbs that target different epitopes, exploit different effector mechanisms or combine directly cytotoxic MAbs with MAbs that rely on immune effector functionality. Such MAbs in combination can exhibit synergistic therapeutic effects. In addition, AXL MAbs can be administered concomitantly with other therapeutic modalities, including but not limited to various chemotherapeutic and biologic agents, androgen-blockers, immune modulators (e.g., IL-2, GM-CSF), surgery or radiation. In a preferred embodiment, the AXL MAbs are administered in conjugated form.

AXL ADC formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the AXL ADC preparation, via an acceptable route of administration such as intravenous injection (IV), typically at a dose in the range, including but not limited to, 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg MAb per week are effective and well tolerated.

Based on clinical experience with the Herceptin® (Trastuzumab) in the treatment of metastatic breast cancer, an initial loading dose of approximately 4 mg/kg patient body weight IV, followed by weekly doses of about 2 mg/kg IV of the MAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the MAbs used, the degree of AXL expression in the patient, the extent of circulating shed AXL antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of AXL in a given sample (e.g. the levels of circulating AXL antigen and/or AXL expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

An object of the present invention is to provide AXL ADCs, which inhibit or retard the growth of tumor cells expressing AXL. A further object of this invention is to provide methods to inhibit angiogenesis and other biological functions and thereby reduce tumor growth in mammals, preferably humans, using such AXL ADCs, and in particular using such AXL ADCs combined with other drugs or immunologically active treatments.

VII.) Combination Therapy

In one embodiment, there is synergy when tumors, including human tumors, are treated with AXL ADCs in conjunction with chemotherapeutic agents or radiation or combinations thereof. In other words, the inhibition of tumor growth by a AXL ADC is enhanced more than expected when combined with chemotherapeutic agents or radiation or combinations thereof. Synergy may be shown, for example, by greater inhibition of tumor growth with combined treatment than would be expected from a treatment of only AXL ADC or the additive effect of treatment with a AXL ADC and a chemotherapeutic agent or radiation. Preferably, synergy is demonstrated by remission of the cancer where remission is not expected from treatment either from a AXL ADC or with treatment using an additive combination of a AXL ADC and a chemotherapeutic agent or radiation.

The method for inhibiting growth of tumor cells using a AXL ADC and a combination of chemotherapy or radiation or both comprises administering the AXL ADC before, during, or after commencing chemotherapy or radiation therapy, as well as any combination thereof (i.e. before and during, before and after, during and after, or before, during, and after commencing the chemotherapy and/or radiation therapy). For example, the AXL ADC is typically administered between 1 and 60 days, preferably between 3 and 40 days, more preferably between 5 and 12 days before commencing radiation therapy and/or chemotherapy. However, depending on the treatment protocol and the specific patient needs, the method is performed in a manner that will provide the most efficacious treatment and ultimately prolong the life of the patient.

The administration of chemotherapeutic agents can be accomplished in a variety of ways including systemically by the parenteral and enteral routes. In one embodiment, the AXL ADCs and the chemotherapeutic agent are administered as separate molecules. Particular examples of chemotherapeutic agents or chemotherapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, gemcitabine, chlorambucil, taxol and combinations thereof.

The source of radiation, used in combination with a AXL ADC, can be either external or internal to the patient being treated. When the source is external to the patient, the therapy is known as external beam radiation therapy (EBRT). When the source of radiation is internal to the patient, the treatment is called brachytherapy (BT).

The above described therapeutic regimens may be further combined with additional cancer treating agents and/or regimes, for example additional chemotherapy, cancer vaccines, signal transduction inhibitors, agents useful in treating abnormal cell growth or cancer, antibodies (e.g. Anti-CTLA-4 antibodies as described in WO/2005/092380 (Pfizer)) or other ligands that inhibit tumor growth by binding to IGF-1R, and cytokines.

When the mammal is subjected to additional chemotherapy, chemotherapeutic agents described above may be used. Additionally, growth factor inhibitors, biological response modifiers, anti-hormonal therapy, selective estrogen receptor modulators (SERMs), angiogenesis inhibitors, and anti-androgens may be used. For example, anti-hormones, for example anti-estrogens such as Nolvadex (tamoxifen) or, anti-androgens such as Casodex (4'-cyano-3-(4-fluorophenylsulphonyl)-2-hydroxy-2-methyl-3-'-(trifluoromethyl)propionanilide) may be used.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

VIII.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise an antibody that is or can be detectably labeled. Kits can comprise a container comprising a Drug Unit.

The kit of the invention will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a cancer of a tissue set forth in Table I.

The terms "kit" and "article of manufacture" can be used as synonyms.

In another embodiment of the invention, an article(s) of manufacture containing compositions, such as antibody(s), or antibody drug conjugates (ADCs) e.g., materials useful for the diagnosis, prognosis, prophylaxis and/or treatment of cancers of tissues such as those set forth in Table I is provided. The article of manufacture typically comprises at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s). In another embodiment a container comprises an antibody, binding fragment thereof or specific binding protein for use in evaluating protein expression of AXL in cells and tissues, or for relevant laboratory, prognostic, diagnostic, prophylactic and therapeutic purposes; indications and/or directions for such uses can be included on or with such container, as can reagents and other compositions or tools used for these purposes.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding AXL or an antibody drug conjugate specifically binding to AXL.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which is intended to limit the scope of the invention.

Example 1

The AXL Antigen

AXL, otherwise know as Tyrol, UFO, and ARK (as well as, GenBank Accession No.: NM_021913) is a protein that encodes a receptor tyrosine kinase with high amino acid similarity to the human trk, eph, eck, and ros proteins, and insulinlike growth factor 1 receptor. The protein encoded by this gene belongs to a transmembrane receptor tyrosine kinase (TRKs) family which includes the Rse/Tyro3 and MER receptors. This family is characterized by a unique extracellular composition of immunoglobulin-like fibronectin III-like domains. These structural findings suggest Axl family members may be involved in both cell adhesion and intracellular signalling. See, Sainaghi, et. al., J. Cell. Phys. 204:36-44 (2005). See also, O'Bryan, et. al., J. Bio. Chem., Vol. 270 no. 2, pp. 551-557 (1995). Also, it has been noted that Axl is expressed in multiple cancers such as lung, breast, ovarian, thyroid, gastric, kidney, colon, and myeloid leukemias. For further reference, see Shieh, et. al., Neoplasia, vol 7, No. 12 pp 1058-1064 (December 2005); Berclaz, et. al. Annals of Oncology, vol. 12 pp. 819-824 (2001); Sun, et. al. Oncology 2004; 66:450-457 (2004); Ito, et. al., Thyroid, vol. 9:No. 6, pp. 563-567 (1999); Wu, et. al., AntiCancer Res., vol. 22, pp. 1071-1078 (2002); Chung, et. al. DNA and Cell Bio., Vol. 22:No. 8, pp. 533-540 (2003); Craven, et. al., Int. J. Cancer, vol. 60 pp. 791-797 (1995). The AXL cDNA is 4,743 bp in length and encodes a 894 amino acid ORF (See, FIG. 1). For exemplary embodiments of the AXL antigen, see FIG. 1.

Example 2

Generation of AXL Monoclonal Antibodies (MAbs)

In one embodiment, diagnostic Monoclonal Antibodies ("mAbs") to AXL comprise those that react with epitopes specific for AXL that would bind to AXL expressed on cells in frozen or paraffin embedded, formalin fixed, tissue sections prepared from patient biopsies. Immunogens for generation of such MAbs include those designed to encode or contain the AXL protein sequence. Immunogens include peptides, recombinant proteins, cells that endogenously express AXL or those that have been engineered to express AXL (such as 293T-AXL).

MAbs to AXL were generated using either VelocImmune® mice or balb/c mice. The mAb designated V77-2a37.1 was generated after immunizing velocimmune mice with recombinant 293T cells expressing AXL. The AXL MAb, V77-2a37.1 specifically binds to AXL expressing cells (recombinant and endogenous) and AXL expressing tumor cells in frozen or paraffin embedded, formalin fixed, tissue sections prepared from patient biopsies.

DNA coding sequences for AXL MAb V77-2a37.1 was determined after isolating mRNA from the respective hybridoma cells with TRIZOL reagent (Life Technologies, Gibco BRL).

Anti-AXL V77-2a37.1 heavy and light chain variable nucleic acid sequences were sequenced from the hybridoma cells using the following protocol. V77-2a37.1 secreting hybridoma cells were lysed with TRIZOL reagent (Life Technologies, Gibco BRL). Total RNA was purified and quantified. First strand cDNAs was generated from total RNA with oligo (dT)12-18 priming using the Gibco-BRL SUPERSCRIPT Preamplification system. First strand cDNA was amplified using human immunoglobulin variable heavy chain primers, and human immunoglobulin variable light chain primers. PCR products were sequenced and the variable heavy and light chain regions determined.

The nucleic acid and amino acid sequences of the full length heavy and light chains are listed in FIGS. 2A and 2B and FIGS. 3A and 3B. Alignment of V77-2a37.1 MAbs to human Ig germline is set forth in FIG. 4A-4B.

Example 3

Human Clinical Trials for the Treatment and Diagnosis of Human Carcinomas Through Use of AXL ADCs AXL ADCs are used in accordance with the present invention which specifically bind to AXL, and are used in the treatment of certain tumors, preferably those listed in Table I. In connection with each of these indications, two clinical approaches are successfully pursued.

I.) Adjunctive therapy: In adjunctive therapy, patients are treated with AXL ADCs in combination with a chemotherapeutic or anti-neoplastic agent and/or radiation therapy or a combination thereof. Primary cancer targets, such as those listed in Table I, are treated under standard protocols by the addition of AXL ADCs to standard first and second line therapy. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents. These dosage reductions allow additional and/or prolonged therapy by reducing dose-related toxicity of the chemotherapeutic or biologic agent. AXL ADCs are utilized in several adjunctive clinical trials in combination with the chemotherapeutic or anti-neoplastic agents.

II.) Monotherapy: In connection with the use of the AXL ADCs in monotherapy of tumors, the AXL ADCs are administered to patients without a chemotherapeutic or anti-neoplastic agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents.

Dosage

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the antibody and/or ADC and the particular therapeutic or prophylactic effect to be achieved, and (b) the limitations inherent in the art of compounding such an active compound for the treatment of sensitivity in individuals.

An exemplary, non limiting range for a therapeutically effective amount of an AXL ADC administered in combination according to the invention is about 0.5 to about 10 mg/kg, about 1 to about 5 mg/kg, at least 1 mg/kg, at least 2 mg/kg, at least 3 mg/kg, or at least 4 mg/kg. Other exemplary non-limiting ranges are for example about 0.5 to about 5 mg/kg, or for example about 0.8 to about 5 mg/kg, or for example about 1 to about 7.5 mg/kg. The high dose embodiment of the invention relates to a dosage of more than 10 mg/kg. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Clinical Development Plan (CDP)

The CDP follows and develops treatments of AXL ADCs in connection with adjunctive therapy or monotherapy. Trials initially demonstrate safety and thereafter confirm efficacy in repeat doses. Trials are open label comparing standard chemotherapy with standard therapy plus AXL ADCs. As will be appreciated, one non-limiting criteria that can be utilized in connection with enrollment of patients is AXL expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAMA response); and, (iii) toxicity to normal cells that express AXL. Standard tests and follow-up are utilized to monitor each of these safety concerns. AXL ADCs are found to be safe upon human administration.

Example 4

Detection of AXL Protein in Cancer Patient Specimens by IHC

Figure 5B:
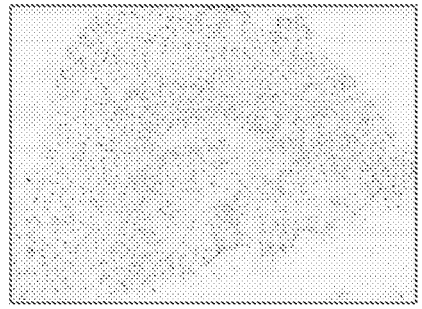
Figure 5C:
Figure 5D:
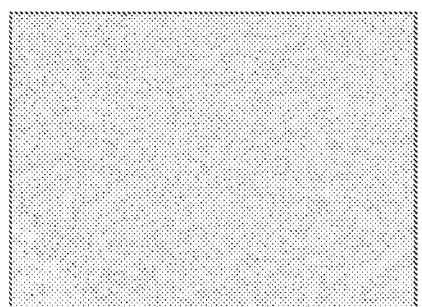
Figure 5E:
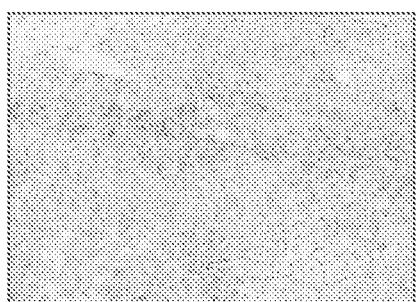
Figure 5F:
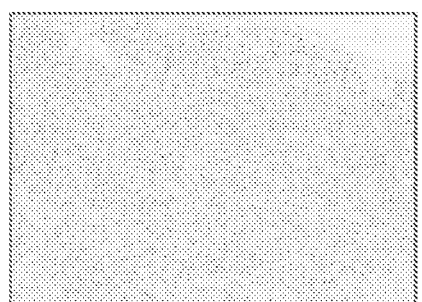
Figure 5G:
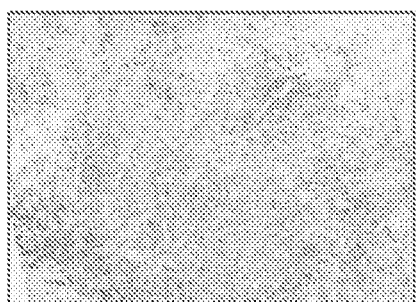
Figure 5H:
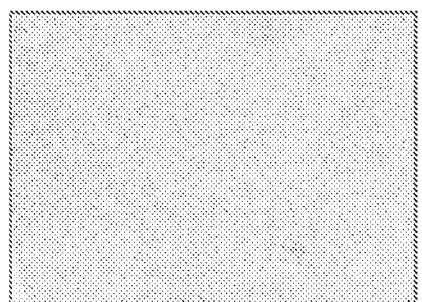
Figure 5I:
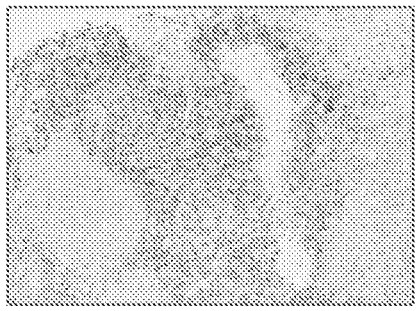
Figure 5J:
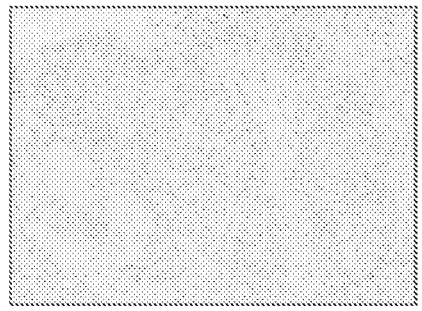

Expression of AXL protein by immunohistochemistry was tested in tumor specimens from sarcoma, pancreatic, melanoma, ovarian, and lung cancer samples. Briefly, formalin fixed, paraffin wax-embedded tissues were cut into four (4) micron sections and mounted on glass slides. The sections were de-waxed, rehydrated, and treated with NOVOCASTRA BOND Epitope Retrieval Solution 2 (Leica Biosystems, Buffalo Grove, Ill.) in the BOND-MAX automated IHC staining system (Leica Biosystems, Buffalo Grove, Ill.) for thirty (30) minutes at 100° C. then placed for twelve (12) minutes at room temperature. Sections were then incubated with either monoclonal mouse anti-AXL antibody denoted V77-2a37.1, or an isotype control. Subsequently, the sections were treated with the NOVOCASTRA BOND Polymer Refine Detection System which consists of incubation in a post-primary rabbit anti-mouse IgG reagent followed by incubation with a polymer anti-rabbit poly-HRP-1gG reagent (Leica Biosystems, Buffalo Grove, Ill.). Sections were then treated with 3% hydrogen peroxide solution to inactivate endogenous peroxidase activity. Chromogen substrate visualization was developed using the DAB refine kit (Leica Biosystems, Buffalo Grove, Ill.), nuclei were stained using hematoxylin, and slides were scanned and analyzed on the APERIO ePathology Scanscope imaging system (Leica Biosystems, Vista, Calif.). Specific staining was detected in patient specimens using the AXL-specific V77-2a37.1 antibody, as indicated by the brown staining. (See, FIGS. 5A, C, E, G, and I). In contrast, the isotype control antibody did not stain the tumor specimen. (See, FIGS. 5B, D, F, H, and J).

The results show expression of AXL in the tumor cells of patient sarcoma (FIG. 5A), pancreatic (FIG. 5C)), melanoma (FIG. 5E), ovarian (FIG. 5G), and lung cancer (FIG. 5I) tissues. These results indicate that AXL is expressed in human cancers and that antibodies directed to this antigen are useful for diagnostic and prognostic purposes. (FIG. 5A-FIG. 5J).

Example 5

Epitope Mapping of V77-2a37.1 MAb

It is known in the art if the epitopes of two antibodies are overlapping, or are in close proximity to one another, then it is anticipated that the antibodies would block each other to an extent determined by the proximity of their epitopes. An antibody competition experiment, in which one antibody is labeled and challenged with a molar excess of unlabeled antibody, then reacted with immobilized target protein, is a facile method for determining whether two antibodies bind to epitopes located in close proximity to one another.

An antibody competition experiment was undertaken to determine whether the anti-AXL antibody of the invention (i.e. V77-2a37.1) interfere with another MAbs which bind AXL, and thus bind to overlapping epitopes.

In this experiment, test antibodies were first biotinylated. The biotinylated antibodies were then challenged with a panel of unlabeled antibodies in an AXL binding assay, all present at a 50 fold molar excess to the biotinylated antibodies. The unlabeled antibody panel included the unlabeled versions of the two test antibodies, a third antibody directed to AXL from Cell Signaling, and an appropriate isotype control. After a two hour incubation period, in which the mixture of biotinylated and unlabeled antibodies were reacted with recombinant human AXL, immobilized onto an ELISA plate, unbound antibody was removed by washing, and immobilized biotin was detected with Streptavidin-HRP followed by TMB substrate solution.

It was expected that the unlabeled version of v77-2a37.1 would block the biotinylated version of itself. The same result was anticipated for the unlabeled and biotinylated versions of other AXL MAbs. However, if the unlabeled version of v77-2a37.1 was found to block the biotinylated version of the other AXL MAbs, or vice versa, the conclusion would be that these antibodies compete with each other, due to their epitopes on the AXL protein being in close proximity. The results obtained with the Cell Signaling antibody would indicate if the epitope of this antibody was distant or in close proximity to that of v77-2a37.1.

Materials and Methods

The protein and antibodies used in this experiment are summarized in Table IV.

BIOTINYLATION OF ANTIBODIES: Aliquots of AXL antibodies v77-2a37.1 and M77-297b81.1.1 were biotinylated using a 20-fold molar ratio of Sulfo-NHS-LC-Biotin (Thermo-Fisher, Waltham, Mass.) for 2 hours at room temperature. Unincorporated biotin was removed by exhaustive dialysis against PBS.

IMMOBILIZATION OF RECOMBINANT AXL: Recombinant human Axl-tag 5 protein was first diluted to 0.5 µg/mL in carbonate buffer. Aliquots of the diluted protein solution (50 µL) were pipetted into the wells of a 96 well NUNC MAXISORP ELISA plate (Thermo-Fisher, Waltham, Mass.). The plate was covered and incubated overnight at room temperature to immobilize the protein. The plate was then aspirated and washed 3 times with PBST (PBS plus 0.05% TWEEN-20), 200 µL per well per wash cycle. The plate was blocked with 200 µL blocking solution (PBS plus 3% non-fat dried milk) for 1 hour at room temperature.

ANTIBODY COMPETITION: The unlabeled antibodies were diluted to a concentration of 100 µg/mL in PBST plus 3% non-fat dried milk, while the two biotinylated antibodies were diluted to a concentration of 2 µg/mL in PBST plus 3% non-fat dried milk. Aliquots (25 µL) of each of the unlabeled antibodies were pipetted into designated wells of the coated plate, followed by 25 µL aliquots of the biotinylated antibodies. The solutions were mixed well, and incubated in the plate for 2 hours at room temperature. The plate was washed 3 times with PBST. Bound biotinylated antibody was detected with 50 µL Streptavidin-HRP (Southern Biotech, Birmingham, Ala.); diluted 1 to 5000 in PBST with 3% non-fat dried milk; 1 hour at room temperature). The plate was then washed 3 times, and bound HRP was detected with 70 µL TMB (20 minutes at room temperature), followed by 50 µL stop solution. The optical density of the plate was then measured at 650 nm.

RESULTS: The results show that in the absence of any unlabeled antibody, the biotinylated versions of both V77-2a37.1 and M77-297b81.1.1 MAbs produced a robust signal with the AXL-coated ELISA plate. This result indicated that the plate was well coated and that the biotinylation reaction produced good results.

Furthermore, the isotype control antibody included in this experiment, cmlys-1c3.1, did not interfere with the ability of the two biotinylated antibodies to bind to AXL, indicating that the isotype control does not compete with either of the two biotinylated antibodies.

As anticipated, the unlabeled version of antibody V77-2a37.1, present at a 50 fold molar excess of the biotinylated version, competes with the biotinylated version of itself for binding to immobilized AXL. Likewise, the unlabeled version of M77-297b81.1.1 competes with the biotinylated version of itself. However, when the biotinylated version of V77-2a37.1 is presented with a 50 fold molar excess of M77-297b81.1.1, no competition is observed, indicating that the epitopes of these two antibodies are indeed distinct. In support of this observation, when the biotinylated version of M77-297b81.1.1 is presented with a 50 fold molar excess of V77-2a37.1, no competition is observed (Table V and FIG. 8).

Figure 8:
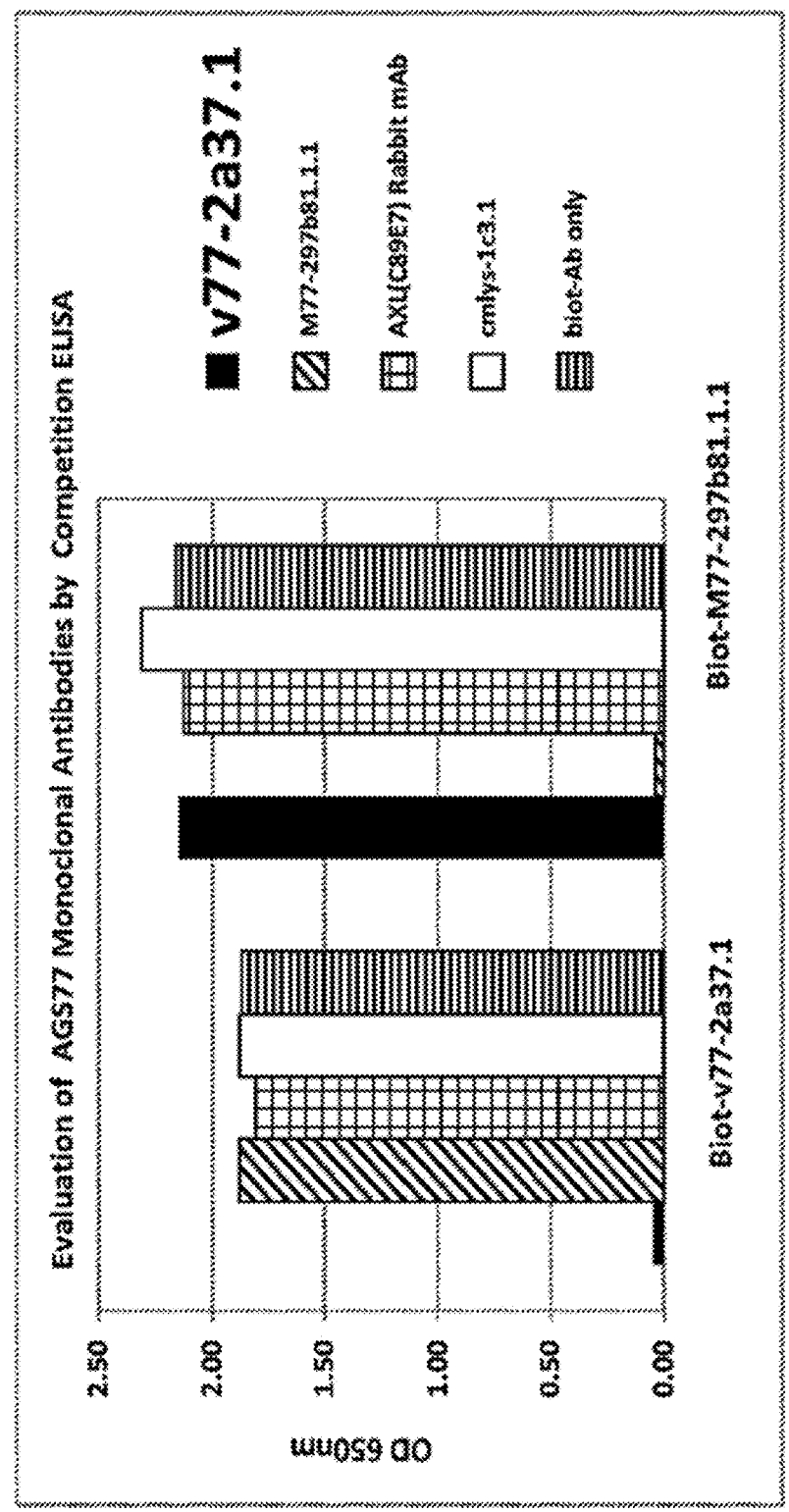
FIG. 8. Graphical summary of the antibody competition experiment (Example 5).

Additionally, this experiment also examined the ability of the Cell Signaling rabbit monoclonal anti-AXL antibody to compete with biotinylated V77-2a37.1 and biotinylated M77-297b81.1.1 MAb. The results presented show indicate that the Cell Signaling rabbit monoclonal anti-AXL antibody has a small impact (3.3% competition) on the ability of biotinylated V77-2a37.1 to bind to AXL, and a similar small impact (1.5%) on the ability of biotinylated M77-297b81.1.1 to bind to AXL. These results suggest the potential of a di minimus degree of overlap between the epitopes of Cell Signaling rabbit monoclonal anti-AXL antibody and the two test antibodies (FIG. 8).

Example 6

Evaluation of C89E7 MAb and AF154 MAb as an Immunohistochemistry Reagent for AXL Detection Using Cell Block Samples In this experiment, three (3) cell block samples, Human lung cancer cell lines NCI-H292 and HCC827 (purchased from American Type Culture Collection), and NCI-H727 (purchased from European Collection of Cell Culture) were fixed in 10% phosphate buffered formalin overnight after cells were cultured in RPMI1640 medium (Thermo Fisher Scientific, Waltham, Mass.), supplemented with 10% Fetal Bovine Serum (Sigma-Aldrich, St. Louis, Mo.), and centrifuged and washed. Then the cell pellets were mixed with O.C.T. Compound (Sakura Finetek Japan) to obtain cell blocks which were subsequently embedded in paraffin.

After cutting the cell blocks and mounting on glass slides, AXL expression in the sections was confirmed by RNA in situ hybridization (RNA ISH) using RNA ISH kit (QUANTIGENE ViewRNA ISH tissue 1-Plex Assay kit (Affymetrix, Santa Clara, Calif.) and QUANTIGENE ViewRNA Chromogenic Signal Amp kit (Affymetrix, Santa Clara, Calif.) with QUANTIGENE ViewRNA TYPE1 Probe Set Human AXL (Affymetrix, Santa Clara, Calif.) according to the provided user manual). To visualize the AXL mRNAs labelled with the alkaline phosphatase (AP), WARP RED Chromogen Kit (Biocare Medical, Concord, Calif.) was used as the chromogen according to the protocol included in the kit. Then the slides were counterstained with hematoxylin, air-dried, cleared in xylene, and mounted with permanent mounting medium ENTELLAN new reagent (Merck, Darmstadt, Germany). Specific signal of AXL expression was observed in the NCI-H292 cells (FIG. 6A(i)) whereas virtually no signal were observed in HCC827 (FIG. 6A(ii)) and NCI-H727 cells (FIG. 6A(iii), indicating NCI-H292 cell line was AXL positive, but both HCC827 and NCI-H727 cell lines were AXL negative.

Next, two anti-AXL antibodies, the Cell Signaling rabbit monoclonal antibody [C89E7] (Cell signaling Technologies, Danvers, Mass.) and the R&D goat polyclonal antibody [AF154] (R&D systems, Minneapolis, Minn.) were evaluated using the cell block samples by immunohistochemistry (IHC). Briefly, the sections of the cell blocks were de-waxed and rehydrated, and antigen retrieval was performed by autoclaving (121° C. for 10 minutes) or microwaving (100° C. for 15 minutes), and then endogenous peroxidase was inactivated with 3% $H_2O_2$-methanol. The slides were then blocked with TBS containing 1% of BSA and incubated with 1:100 diluted antibodies in the same buffer. After three (3) times of wash with TBST (TBS plus 0.05% Tween 20), the AXL in the slides was detected and visualized with the second antibody and 3,3'-Diaminobenzidine, tetrahydrochloride (DAB) reagent listed in Table VII, before being counterstained with Mayer's hematoxylin. The detailed conditions used in the IHC experiments are described in Table VII. The results of IHC staining of AXL on these three cell blocks were shown in FIG. 6B(i) (vi). The IHC for AXL with anti-AXL monoclonal antibody [C89E7] in NCI-H292 cells showed intense stainings (FIG. 6B(i)), but virtually no stainings were observed in HCC827 (FIG. 6B(ii)) and NCI-H727 cells (FIG. 6B(iii)), which was consistent with the results of AXL expression observation obtained by RNA ISH experiments, whereas the marginal or weak IHC staining signal were observed in HCC827 (FIG. 6B(v)) and NCI-H727 (FIG. 6B(vi)) cells by anti-AXL polyclonal antibody [AF154], which was not consistent with the RNA ISH results. These observations suggested that anti-AXL monoclonal antibody [C89E7] appeared to be more suitable as a IHC reagent than anti-AXL polyclonal antibody [AF154] since anti-AXL monoclonal antibody [C89E7] did not show non-specific signal as observed in these experiments using these three cell blocks.

Example 7

Comparative Immunohistochemistry in Selected AXL RNA (+) (−) FFPE Samples Using anti-AXL V77-2a37.1 MAb, M77-297b81.1.1 MAb, and C89E7 MAb Non-specific IHC staining with anti-AXL antibodies V77-2a37.1, M77-297b81.1.1 (ATCC Designation PTA-122092), and AXL (C89E7) was evaluated in AXL-negative tumor specimens (measured by qPCR) from breast (FIGS. 7A-7D), hepatocellular (FIGS. 7E-7H), and colon (FIGS. 7I-7L) carcinoma samples.

Briefly, formalin fixed, paraffin wax-embedded tissues were cut into 4 micron sections and mounted on glass slides. The sections were de-waxed, rehydrated and treated with NOVOCASTRA BOND Epitope Retrieval Solution 2 (Leica Biosystems, Buffalo Grove, Ill.) in the BOND-MAX automated IHC staining system (Leica Biosystems, Buffalo Grove, Ill.) for 30 minutes at 100° C. then for 12 minutes at room temperature. Sections were then incubated with monoclonal anti-AXL antibody V77-2a37.1, M77-297b81.1, monoclonal rabbit anti-AXL antibody Axl (C89E7) (Cell Signaling Technology, Danvers, Mass.), or an isotype control. Subsequently, the sections were treated with the NOVOCASTRA BOND Polymer Refine Detection System which consists of incubation in a post-primary rabbit anti-mouse IgG reagent followed by incubation with a polymer anti-rabbit poly-HRP-IgG reagent (Leica Biosystems, Buffalo Grove, Ill.). Sections were then treated with 3% hydrogen peroxide solution to inactivate endogenous peroxidase activity. Chromogen substrate visualization was developed using the DAB refine kit (Leica Biosystems, Buffalo Grove, Ill.), nuclei were stained using hematoxylin, and slides were scanned and analyzed on the APERIO ePathology Scanscope imaging system (Leica Biosystems, Vista, Calif.).

Figure 7A:
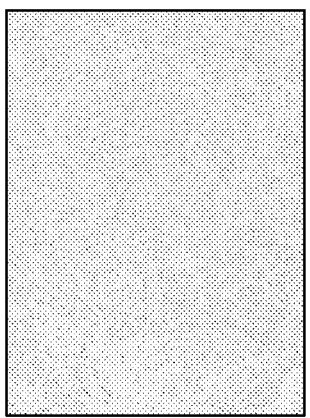
FIGS. 7A-7L. Anti-AXL antibody immunohistochemistry (IHC) comparison in AXL-negative cancer specimens. Detection of AXL non-specific IHC staining in breast (FIGS. 7A-7D), hepatocellular (FIGS. 7E-7H), and colon (FIGS. 7I-7L) carcinoma specimens. IHC assay performed with V77-2a37.1 (FIGS. 7A, 7E, 7I), M77-297b81.1.1 (FIGS. 7B, 7F, 7J), AXL (C89E7) (FIGS. 7C, 7G, 7K), and mouse IgG1 negative control antibody (FIGS. 7D, 7H, 7L). The results showed more non-specific IHC staining with AXL (C89E7) in cancer specimens with limited AXL mRNA expression (FIGS. 7C, 7G, 7K; see arrows).
Figure 7E:
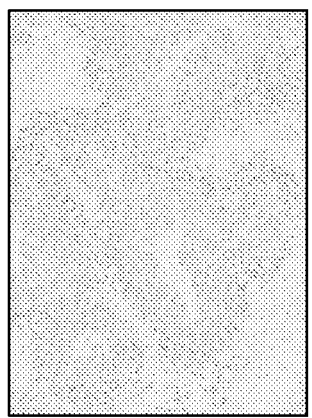
Figure 7I:
Figure 7B:
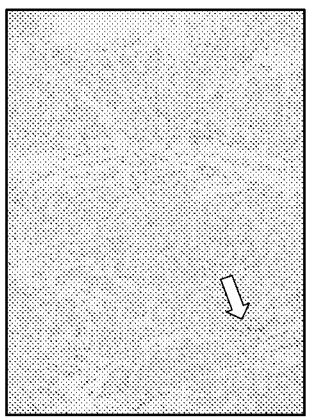
Figure 7F:
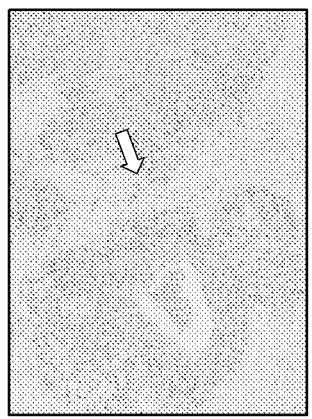
Figure 7J:
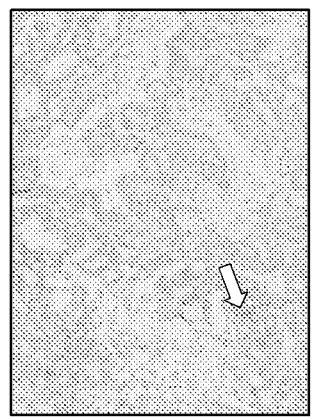
Figure 7C:
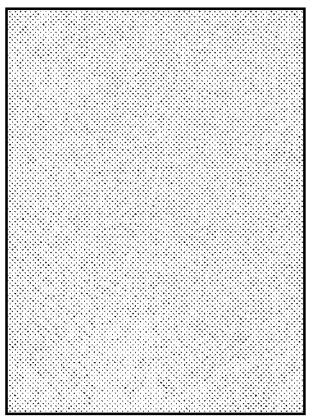
Figure 7G:
Figure 7K:
Figure 7D:
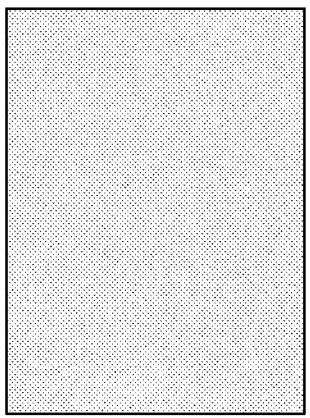
Figure 7H:
Figure 7L:

The results show the limited or absence of non-specific staining was observed in all of the tumor specimens using the AXL-specific V77-2a37.1 (FIGS. 7A, 7E, 7I) and M77-297b81.1.1 (FIGS. 7B, 7F, 7J) antibodies, as indicated by the lack of brown staining. Furthermore, the isotype control antibody also did not exhibit non-specific staining in the tumor specimens (FIGS. 7D, 7H, 7L). In contrast, the commercially available anti-AXL antibody, AXL (C89E7), exhibited noticeable brown staining (FIGS. 7C, 7G, 7K, see arrows) in the tumor specimens with limited AXL mRNA expression.

The results in FIGS. 7A-7L indicate that V77-2a37.1 and M77-297b81.1.1 are superior IHC antibodies due to the absence of non-specific staining in AXL mRNA negative tissue samples.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Tables

TABLE I

Tissues/Cells that express AXL when malignant.

Lung;
Ovarian;
Melanoma;
Pancreatic;
Sarcoma.

TABLE II

Amino Acid Abbreviations

| SINGLE LETTER | THREE LETTER | FULL NAME |
| --- | --- | --- |
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Amino Acid Substitution Matrix
Adapted from the GCG Software 9.0 BLOSUM62 amino acid substitution matrix (block substitution matrix). The higher the value, the more likely a substitution is found in related, natural proteins.

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | 2 | 1 | 2 | 0 | 2 | 1 | 1 | 1 | 1 | 2 | 1 | 1 | 1 | 0 | 0 | -3 | -2 | | A |
|   | 9 | 3 | 4 | 2 | 3 | 3 | 1 | 3 | 1 | 1 | 3 | 3 | 3 | 3 | 1 | 1 | 1 | 2 | 2 | C |
|   |   | 6 | 2 | 3 | 1 | 1 | 3 | 1 | 4 | 3 | 1 | 1 | 0 | 2 | 0 | 1 | 3 | 4 | 3 | D |
|   |   |   | 5 | -3 | -2 | 0 | -3 | 1 | -3 | -2 | 0 | -1 | 2 | 0 | 0 | -1 | -2 | -3 | -2 | E |
|   |   |   |   | 6 | -3 | -1 | 0 | -3 | 0 | 0 | 3 | 4 | 3 | 3 | 2 | 2 | 1 | 1 | 3 | F |
|   |   |   |   |   | 6 | 2 | 4 | 2 | 4 | 3 | 0 | 2 | 2 | 2 | 0 | 2 | 3 | 2 | 3 | G |
|   |   |   |   |   |   | 8 | -3 | -1 | -3 | -2 | 1 | -2 | 0 | 0 | -1 | -2 | -3 | -2 | 2 | H |
|   |   |   |   |   |   |   | 4 | -3 | 2 | 1 | 3 | 3 | 3 | 3 | 2 | 1 | 3 | 3 | 1 | I |
|   |   |   |   |   |   |   |   | 5 | -2 | -1 | 0 | -1 | 1 | 2 | 0 | -1 | -2 | -3 | -2 | K |
|   |   |   |   |   |   |   |   |   | 4 | 2 | 3 | 3 | 2 | 2 | 2 | 1 | 1 | 2 | 1 | L |
|   |   |   |   |   |   |   |   |   |   | 5 | -2 | -2 | 0 | -1 | -1 | -1 | 1 | -1 | -1 | M |
|   |   |   |   |   |   |   |   |   |   |   | 6 | -2 | 0 | 0 | 1 | 0 | -3 | -4 | -2 | N |
|   |   |   |   |   |   |   |   |   |   |   |   | 7 | 1 | 2 | 1 | 1 | 2 | 4 | 3 | P |
|   |   |   |   |   |   |   |   |   |   |   |   |   | 5 | 1 | 0 | -1 | -2 | -2 | -1 | Q |
|   |   |   |   |   |   |   |   |   |   |   |   |   |   | 5 | 1 | 1 | 3 | 3 | 2 | R |
|   |   |   |   |   |   |   |   |   |   |   |   |   |   |   | 4 | 1 | -2 | -3 | -2 | S |
|   |   |   |   |   |   |   |   |   |   |   |   |   |   |   |   | 5 | 0 | -2 | -2 | T |
|   |   |   |   |   |   |   |   |   |   |   |   |   |   |   |   |   | 4 | -3 | -1 | V |
|   |   |   |   |   |   |   |   |   |   |   |   |   |   |   |   |   |   | 11 | 2 | W |
|   |   |   |   |   |   |   |   |   |   |   |   |   |   |   |   |   |   |   | 7 | Y |

TABLE IV

Description of the Recombinant AXL Protein and Antibodies used in the Competition Experiment (Example 5).

| Description | Name | Source | Lot | Stock Concentration (mg/ml) |
|---|---|---|---|---|
| Recombinant Human Axl Protein | Axl-tag 5 | Agensys, Inc. | DT1040 | 1.67 |
| Mouse anti-Hu Axl monoclonal antibody (purified) | v77-2a37.1 | Agensys, Inc. | RC2933 | 2.05 |
| Mouse anti-Hu Axl monoclonal antibody (purified) | M77-297b81.1.1 | Agensys, Inc. | RC5481 | 5.66 |
| Rabbit anti-Hu Axl monoclonal antibody (purified) | AXL(C89E7) | Cell Signaling | Lot 4 | 0.16 |
| Mouse anti-Lysozyme monoclonal antibody (purified) | cmlys-1c3.1 | Agensys, Inc. | RC3265 | 2.16 |

TABLE V

Summary of the Antibody Competition Experiment (Example 5).

| Unlabeled Antibody (50 µg/mL) | Biot-v77-2a37.1 (1 µg/mL) OD (650 nm) | Biot-v77-2a37.1 (1 µg/mL) % competition | Biot-M77-297b81.1.1 (1 µg/mL) OD (650 nm) | Biot-M77-297b81.1.1 (1 µg/mL) % competition |
|---|---|---|---|---|
| v77-2a37.1 | 0.04 | 97.7% | 2.15 | 0.6% |
| M77-297b81.1.1 | 1.88 | 0.0% | 0.04 | 98.2% |
| AXL(C89E7) | 1.81 | 3.3% | 2.13 | 1.5% |
| cmlys-1c3.1 | 1.88 | 0.0% | 2.31 | 0.0% |
| biot-Ab only | 1.87 | | 2.16 | |
| blank | 0.04 | | 0.04 | |

TABLE VI

Positions CDR-L1, CDR-L2, CDR-L3 and CDR-H1, CDR-H2, CDR-H3 as identified by the Kabat, Chothia, and Contact schemes, respectively. For CDR-H1, residue numbering is given listed using both the Kabat and Chothia numbering schemes.

| CDR | Kabat | Chothia | Contact |
|---|---|---|---|
| CDR-L1 | L24-L34 RASQSISNWLA (SEQ ID NO: 11) | L24-L34 RASQSISNWLA (SEQ ID NO: 14) | L30-L36 SNWLAWY (SEQ ID NO: 17) |

TABLE VI-continued

Positions CDR-L1, CDR-L2, CDR-L3 and CDR-H1,
CDR-H2, CDR-H3 as identified by the Kabat,
Chothia, and Contact schemes, respectively.
For CDR-H1, residue numbering is given listed
using both the Kabat and Chothia numbering schemes.

| CDR | Kabat | Chothia | Contact |
|---|---|---|---|
| CDR-L2 | L50-L56<br>KASSLES<br>(SEQ ID NO: 12) | L50-L56<br>KASSLES<br>(SEQ ID NO: 15) | L46-L55<br>LLIYKASSLE<br>(SEQ ID NO: 18) |
| CDR-L3 | L89-L97<br>QQYNSYYT<br>(SEQ ID NO: 13) | L89-L97<br>QQYNSYYT<br>(SEQ ID NO: 16) | L89-L96<br>QQYNSYY<br>(SEQ ID NO: 19) |
| CDR-H1* | H31-H37<br>NSSYHWG<br>(SEQ ID NO: 20) | H26-H34<br>GVSITNSSY<br>(SEQ ID NO: 24) | H30-H35B<br>TNSSYHWG<br>(SEQ ID NO: 28) |
| CDR-H1** | H31-H35<br>NSSYHWG<br>(SEQ ID NO: 21) | H26-H32<br>GVSITNSSY<br>(SEQ ID NO: 25) | H30-H35<br>TNSSYHWG<br>(SEQ ID NO: 29) |
| CDR-H2 | H50-H65<br>SIFYNGNTFFNPSLKS<br>(SEQ ID NO: 22) | H52-H56<br>FYNGN<br>(SEQ ID NO: 26) | H47-H58<br>WIGSIFYNGNTF<br>(SEQ ID NO: 30) |
| CDR-H3 | H95-H102<br>QDNWNFRHYFNY<br>(SEQ ID NO: 23) | H95-H102<br>QDNWNFRHYFNY<br>(SEQ ID NO: 27) | H93-H101<br>ERQDNWNFRHYFN<br>(SEQ ID NO: 31) |

*Kabat Numbering
**Chothia Numbering

TABLE VII

| IHC reagents and protocols | | | | | | | | |
|---|---|---|---|---|---|---|---|---|
| Antibodies | Antigen retrieval | | Condition | Detection System/Condition | | Chromogen/Condition | | |
| AXL [C89E7]<br>(Cell Signaling<br>Technology) | Citrate buffer,<br>pH 6.0 | 121° C.,<br>10 min | 1:100<br>RT<br>2 hr. | EnVision+ System-HRP<br>Labelled Polymer Anti-<br>Rabbit (DAKO) | RT,<br>30 min | ImmPACT ™<br>DAB (Vector<br>Laboratories) | 2-fold<br>dilution<br>2 min |
| AXL [AF1541]<br>(R&D Systems) | Immunosaver<br>(Nisshin EM) | 100° C.,<br>15 min | 1:100<br>RT<br>2 hr. | anti-Goat IgG H&L<br>(Rabbit) Antibody,<br>Peroxidase conjugated<br>(Rockland<br>Immunochemicals Inc.) | 1:200,<br>RT<br>30 min | DAB TRIS tablet<br>(MUTO PURE<br>CHEMICALS<br>CO., LTD. | 1 min |

The invention claimed is:

1. An antibody or antigen binding fragment thereof which binds to AXL receptor tyrosine kinase (AXL), wherein the antibody or fragment comprises a heavy chain variable region comprising heavy chain complementarity determining region 1 (CDR-H1), CDR-H2, and CDR-H3 of the amino acid sequence set forth in SEQ ID NO: 8 and a light chain variable region comprising light chain complementarity determining region 1 (CDR-L1), CDR-L2, and CDR-L3 of the amino acid sequence set forth in SEQ ID NO: 10.

2. An antibody or antigen binding fragment of claim 1, wherein the antibody or antigen binding fragment comprises a heavy chain variable region consisting of the amino acid sequence set forth in SEQ ID NO: 8, and a light chain variable region consisting of the amino acid sequence set forth in SEQ ID NO: 10.

3. An antibody of claim 1, wherein the antibody comprises a heavy chain consisting of the amino acid sequence set forth in SEQ ID NO: 7, and a light chain consisting of the amino acid sequence set forth in SEQ ID NO: 9.

4. The antigen binding fragment of claim 1, wherein the fragment is an antigen binding fragment (Fab), F(ab')₂, variable fragment (Fv) or single chain variable fragment (scFv).

5. The antibody of claim 1, wherein the antibody is a fully human antibody.

6. The antibody or antigen binding fragment of claim 1, which the antibody or antigen binding fragment is recombinantly produced.

7. The antibody or antigen binding fragment of claim 1, wherein the antibody or antigen binding fragment is conjugated to an imaging agent.

8. The antibody or antigen binding fragment of claim 1, wherein the antibody or antigen binding fragment is used as a companion diagnostic (CDx) to screen patients for the treatment and management of cancer.

9. A method of detecting AXL expression in a subject comprising a step of contacting the antibody or antigen binding fragment of claim 1 with a sample obtained from the subject.

10. The method of claim 9, which comprises a step of obtaining a sample from the subject.

11. The method of claim 9, wherein the subject is a cancer patient.

12. The method of claim 11, wherein the cancer is selected from the group consisting of sarcoma, pancreatic cancer, melanoma, ovarian cancer, and lung cancer.

13. A method for identifying a cancer patient which is positive for AXL expression, which comprises a step of contacting the antibody or antigen binding fragment of claim 1 with a sample obtained from the cancer patient.

14. The method of claim 13, which comprises a step of obtaining a sample from the cancer patient.

15. The method of claim 13, wherein the cancer is selected from the group consisting of sarcoma, pancreatic cancer, melanoma, ovarian cancer, and lung cancer.

16. The method of claim 13, wherein the cancer patient has undergone treatment by EGFR inhibitor.

17. The method of claim 13, wherein the cancer is resistant to epidermal growth factor receptor (EGFR inhibitor.

18. A kit for detecting AXL expression comprising the antibody or antigen binding fragment of claim 1.

* * * * *